United States Patent
Israels et al.

(10) Patent No.: US 8,859,607 B2
(45) Date of Patent: Oct. 14, 2014

(54) CRYSTALLINE COMPLEXES OF AGRICULTURALLY ACTIVE ORGANIC COMPOUNDS

(75) Inventors: Rafel Israels, Cologne (DE); Heidi Emilia Saxell, Ludwigshafen (DE); Matthias Bratz, Maxdorf (DE); Marco Kuhns, Hassloch (DE); Peter Erk, Frankenthal (DE)

(73) Assignee: BASF SE, Ludwigshafen (DE)

( * ) Notice: Subject to any disclaimer, the term of this patent is extended or adjusted under 35 U.S.C. 154(b) by 665 days.

(21) Appl. No.: 12/526,351

(22) PCT Filed: Feb. 8, 2008

(86) PCT No.: PCT/EP2008/051562
§ 371 (c)(1),
(2), (4) Date: Aug. 7, 2009

(87) PCT Pub. No.: WO2008/096005
PCT Pub. Date: Aug. 14, 2008

(65) Prior Publication Data
US 2010/0113543 A1 May 6, 2010

(30) Foreign Application Priority Data
Feb. 9, 2007 (EP) .................................... 07102083

(51) Int. Cl.
*A01N 43/653* (2006.01)
*A01N 43/56* (2006.01)
*A01N 43/20* (2006.01)
*C07D 231/22* (2006.01)
*C07D 405/06* (2006.01)
*C07D 249/08* (2006.01)
*C07D 417/06* (2006.01)
*A01N 47/34* (2006.01)

(52) U.S. Cl.
CPC ............ *C07D 417/06* (2013.01); *C07D 231/22* (2013.01); *A01N 47/34* (2013.01); *A01N 43/56* (2013.01); *C07D 405/06* (2013.01); *A01N 43/653* (2013.01); *C07D 249/08* (2013.01); *A01N 43/20* (2013.01)
USPC ..... 514/407; 514/383; 548/371.1; 548/268.8; 548/262.2

(58) Field of Classification Search
CPC .. C07D 231/22; C07D 405/06; C07D 249/08; A01N 43/653; A01N 43/56; A01N 43/20
USPC .......... 514/407, 383; 548/371.1, 268.8, 262.2
See application file for complete search history.

(56) References Cited

U.S. PATENT DOCUMENTS

| | | | | |
|---|---|---|---|---|
| 4,906,652 A | * | 3/1990 | Karbach et al. | 514/383 |
| 5,869,517 A | * | 2/1999 | Muller et al. | 514/407 |
| 5,968,964 A | * | 10/1999 | Rehnig et al. | 514/383 |
| 6,869,914 B2 | | 3/2005 | Bratz et al. | |
| 2003/0224006 A1 | | 12/2003 | Zaworotko et al. | |

FOREIGN PATENT DOCUMENTS

| | | |
|---|---|---|
| EP | 0 677 246 | 10/1995 |
| JP | 63 068502 | 3/1988 |
| WO | WO 03/074474 | 9/2003 |
| WO | WO 2004/078161 | 9/2004 |
| WO | WO 2004/078163 | 9/2004 |
| WO | WO 2005/089511 | 9/2005 |
| WO | WO 2006/007448 | 1/2006 |

OTHER PUBLICATIONS

Schultheiss et al. Crystal Growth & Design 2009, 9, 2950-2967.*
International Search Report completed Apr. 3, 2008, in International Application No. PCT/EP2008/051562, filed Feb. 8, 2008.
Almarsson, Oern et al., "Crystal engineering of the composition of pharmaceutical phases. Do pharmaceutical co-crystals represent a new path to improved medicines?", Chem. Commun., 2004, p. 1889-1896.
Braga, Dario et al., "Making crystals from crystals: a green route to crystal engineering and polymorphism", Chem. Commun., 2005, pp. 3635-3645.
Database WPI Section Ch. Week 198818—Derwent Publications Ltd., London, GB AN 1988-123634 XP 002474998 and JP 63 068502, 1988.
International Preliminary Report on Patentability dated Aug. 11, 2009, from corresponding International Application No. PCT/EP2008/051562, filed Feb. 8, 2008.
Schultheiss, Nate et al. "Pharmaceutical Cocrystals and Their Physicochemical Properties", Crystal Growth and Design, 2009, p. 2950-2967, vol. 9, No. 6.

* cited by examiner

*Primary Examiner* — Joseph Kosack
*Assistant Examiner* — Matthew Coughlin
(74) *Attorney, Agent, or Firm* — Brinks Gilson & Lione

(57) ABSTRACT

The present invention relates to crystalline complexes comprising at least one agriculturally active organic compound A having at least one functional moiety which is capable as serving as a hydrogen acceptor in a hydrogen bond and thiophanate-methyl.

15 Claims, 6 Drawing Sheets

CRYSTALLINE COMPLEXES OF AGRICULTURALLY ACTIVE ORGANIC COMPOUNDS

Figure 1:
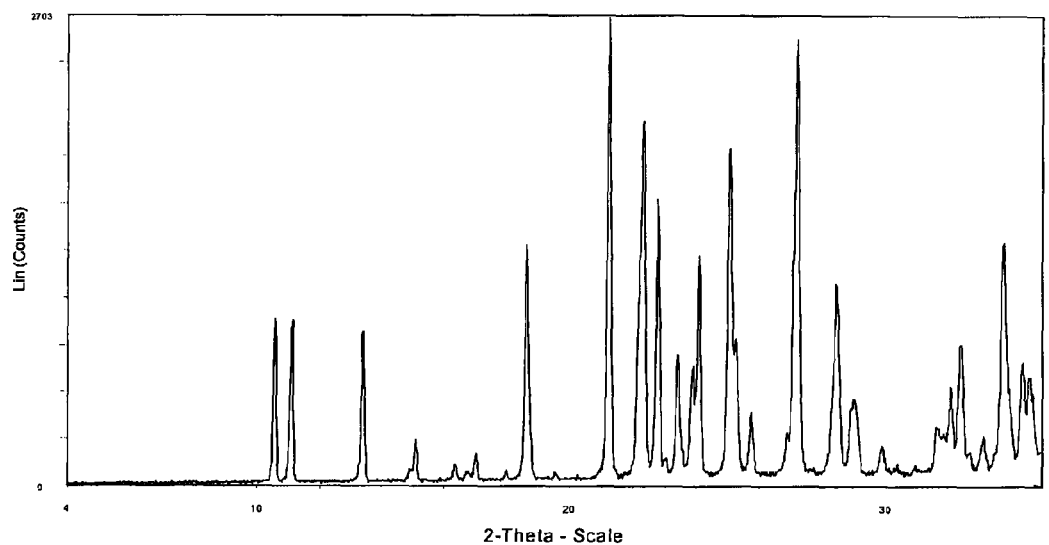

This application is a National Stage application of International Application No. PCT/EP2008/051562, filed Feb. 8, 2008. This application also claims the benefit under 35 U.S.C. §119 of European Patent Application No. 07102083.8, filed Feb. 9, 2007.

The present invention relates to crystalline complexes of at least one agriculturally active organic compound A having at least one functional moiety which is capable of serving as a hydrogen acceptor in a hydrogen bond.

Agriculturally active organic compounds such as fungicides, herbicides and insecticides or acaricides are usually marketed as liquid or solid formulations which comprise one or more agriculturally active organic compounds and suitable formulation additives. For several reasons, formulation types are preferred, wherein the agriculturally active organic compound (A) is present in the solid state, examples including solid formulations such as dusts, powders or granules and liquid formulations such as suspension concentrates, i.e. liquid formulations containing solid particles of the active organic compound suspended in a liquid suspension medium.

For formulation purposes the agriculturally active organic compound should be a crystalline material having a sufficiently high melting point. Unfortunately, a large number of such organic compounds are amorphous material and/or have low melting points. Such compounds are difficult to formulate as suspension concentrates (SC) in a conventional manner, since the grinding apparatus will get stuck during grinding as a result of the tackiness of the active compound. Formulations of amorphous solid organic compounds are often instable with regard to phase-separation. For example, suspension concentrates of amorphous solid actives tend to become inhomogeneous by segregation of the active organic compound as a result of particle aggregation or particle growth.

Crystalline complexes of organic compounds, also termed as co-crystals are multi-component crystals or crystalline material that consist of at least two different organic compounds which are usually solid at 25° C. or at least a non-volatile oil (vapour pressure less than 1 mbar at 25° C.). In the crystalline complexes (or co-crystals) at least two different organic compounds form a crystalline material having a defined crystal structure, i. e. the at least two organic compounds have a defined relative spatial arrangement within the crystal structure, thereby forming a supra-molecular structure.

In the co-crystals the at least two different compounds interact by non-covalent bonding such as hydrogen bonds and, possibly, other non-covalent intermolecular forces, including π-stacking and van der Waals interaction. Hydrogen bonding is a directional and relatively strong interaction and due to these two properties it is often the dominant force in also molecular recognition through out the nature, for example in formation of DNA, folding of proteins in general, receptors etc. Thus, hydrogen bonding is the force considered in approaches where novel multi-component materials or co-crystals are being designed and described in the literature (see for example D. Braga et al., Chem. Commun., 2005, pp. 2635-3645 and O. Almarsson et al., Chem. Commun., 2004, pp. 1889-1896. However, other intermolecular forces may also be responsible for molecular recognition.

Although the packing in the crystalline lattice cannot be designed or predicted, several supramolecular synthons could successfully recognized in co-crystals. The term "supramolecular synthon" has to be understood as an entity of usually two compounds that are hydrogen bonded together. In co-crystals these synthons further pack in the crystalline lattice to form a molecular crystal. Molecular recognition is one condition of the formation of the synthon. However, the co-crystal must also be energetically favourable, i.e. an energy win in the formation of the co-crystal is also required, as molecules typically can pack very efficiently as crystals of pure components thereby hindering the co-crystal formation.

In co-crystals, usually one of the organic compounds serves as a co-crystal former, i. e. a compound which itself easily forms a crystalline material and which is capable of forming co-crystals with several other organic compounds which themselves may not necessarily form a crystalline phase.

Crystalline complexes of active pharmaceutical compounds have been described in the art on various occasions, e. g. in US2003/224006, WO03/074474, WO2005/089511, EP1608339, EP1631260 and WO2006/007448.

Thiophanate methyl is a well known crystalline fungicide compound of the formula

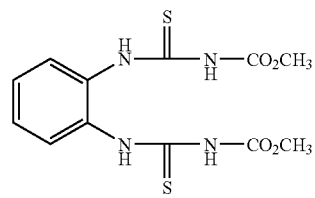 [SMILES: COC(=O)NC(=S)Nc1ccccc1NC(=S)NC(=O)OC]

which melts above 172° C. under decomposition. Thiophanate methyl has protective and curative action against a wide range of fungal pathogens. The thiophanate molecule is degraded in the plant to carbendazim and therefore it belongs to the group of benzimidazole fungicides.

The inventors of the present invention surprisingly found out that thiophanate-methyl is a suitable co-crystal former which forms crystalline complexes with a large number of agriculturally active organic compounds having at least one functional moiety which is capable of serving as a hydrogen acceptor in a hydrogen bond.

Therefore, the present invention relates to crystalline complexes comprising at least one agriculturally active organic compound A having at least one functional moiety which is capable as serving as a hydrogen acceptor in a hydrogen bond and thiophanate-methyl.

The crystalline complexes according to the present invention have a defined crystal structure and have a reasonable high melting point which facilitates the incorporation of such complexes into solid or liquid formulations wherein the active material is present in the solid state. Moreover, the formulations of such crystalline complexes show increased stability, in particular in comparison with formulations containing a mixture of thiophanate methyl and compound A as individual solid compounds.

It is presumed that the formation of the crystalline complexes according to the present invention results from the incapability of thiophanate methyl to achieve effective hydrogen bonds for all hydrogen donors and effective packing of the molecules in the crystalline state at the same time. Therefore at least one of the N-bound hydrogen atoms of the thio-urea unit in the thiophanate molecule forms a hydrogen bond with the at least one hydrogen acceptor moiety in the agriculturally active compound A and/or the thiophanate molecules form a grid-like structure with cavities, wherein the active compound A molecules are included.

Functional groups or moieties, which are capable of being a hydrogen acceptor in a hydrogen bond include oxygen atoms, such as oxygen atoms in an ether moiety, in particular an oxirane group, in a hydroxyl group, in a carbonyl group, in a carboxyl group, in a carboxyamido group, and nitrogen atoms, in particular in the form of primary, secondary or tertiary amino groups or as imino-nitrogen atoms, i.e. =N—.

Preferably, the compound A comprises at least one, e.g. 1, 2, 3 or 4 imino-nitrogen atoms as functional groups or moieties, which are capable of being a hydrogen acceptor in a hydrogen bond. The imino-nitrogen atom may be part of a cyclic or acyclic moiety such as a heterocyclic ring, an oximino moiety or an amidino moiety. Of course, the compound A may carry one or further atoms or moieties, which are capable of acting as a hydrogen acceptor in a hydrogen bond.

In particular, the compound A comprises at least one functional moiety being capable of being a hydrogen acceptor in a hydrogen bond which contains at least one imino-nitrogen which is a ring member in an 5- or 6-membered aromatic or partially unsaturated heterocyclic ring, such as pyridine, pyrimidine, imidazole or imidazoline such as 1H-imidazole, 2H-imidazole, 4,5-dihydro-1H-imidazole, 2,5-dihydro-1H-imidazole, pyrazole or pyrazoline such as 1H-pyrazole, 4,5-dihydro-1H-pyrazole and triazole rings such as 1H-1,2,4-triazole, 1H-1,3,4-triazole and 1H-1,2,3-triazol rings, in particular pyrazole or triazole ring. The heterocyclic ring may be unsubstituted or substituted, e.g. by 1, 2 or 3 substituent radicals. Suitable substituent radicals are in particular those which do not exert an electron withdrawing mesomeric (-M) effect such as nitro, carboxylate, sulfonyl or cyano. Suitable substituent radicals include halogen, $C_1$-$C_6$-alkoxy, $C_1$-$C_4$-haloalkyl, $C_1$-$C_4$-haloalkoxy or phenyl, which itself may be substituted or substituted by 1, 2, 3 or 4 radicals selected from $C_1$-$C_6$-alkyl, halogen, $C_1$-$C_6$-alkoxy, $C_1$-$C_4$-haloalkyl and $C_1$-$C_4$-haloalkoxy, and $C_1$-$C_6$-alkyl, which may be unsubstituted or substituted by one radical selected from alkoxy, cyano, phenyl, $C_1$-$C_4$-alkylcarbonyl, $C_1$-$C_4$-alkoxycarbonyl, carboxyl, carboxamido, $C_1$-$C_4$-alkylaminocarbonyl, $C_1$-$C_4$-dialkylaminocarbonyl and $C_1$-$C_4$-alkylcarbonylamino. It has to be understood that the substituted or unsubstituted 5- or 6-membered aromatic or partially unsaturated heterocyclic ring itself may be part of a larger molecule.

Likewise preferably, the imino-nitrogen may be part of an acyclic oximino moiety such as an imino-ether group =N—O—R or an amidino group C(N=R)NR'$_2$, wherein R and R' independently of each other are selected from hydrogen, $C_1$-$C_6$-alkyl, $C_2$-$C_6$-alkenyl or $C_2$-$C_6$-alkinyl.

Preferably the compound A comprises a functional moiety which is selected from a 5- or 6-membered aromatic heterocyclic radical, such as pyridinyl, pyrimidinyl, 1H-imidazolyl, 1H-pyrazole, 4,5-dihydro-1H-pyrazolyl, and triazolyl, such as 1H-1,2,4-triazolyl, 4H-1,2,4-triazolyl(=1H-1,3,4-triazolyl), 1H-1,2,3-triazolyl and 2H-1,2,3-triazolyl rings, preferably a pyrazolyl or triazolyl radical, in particular a 1H-pyrazolyl or a 1H-1,3,4-triazolyl radical, which may be substituted or substituted as defined above. Preferred substituent radicals include halogen, $C_1$-$C_6$-alkyl, $C_1$-$C_6$-alkoxy, $C_1$-$C_4$-haloalkyl, $C_1$-$C_4$-haloalkoxy or phenyl, which itself may be substituted or substituted by 1, 2, 3 or 4 radicals selected from $C_1$-$C_6$-alkyl, halogen, $C_1$-$C_5$-alkoxy, $C_1$-$C_4$-haloalkyl and $C_1$-$C_4$-haloalkoxy, in particular from halogen or methyl. In particular the compound A comprises one functional moiety, which is selected from imidazol-2-yl, pyrazol-1-yl, pyrazol-3-yl, 1,2,4-triazole-3-yl or 1,2,4-triazole-1-yl, wherein Het is unsubstituted or may carry 1 or 2 radicals selected from halogen atoms and $C_1$-$C_4$-alkyl and/or 1 phenyl group, which may carry 1, 2 or 3 halogen atoms.

In a preferred embodiment of the invention the compound A carries an optionally substituted phenyl ring, in addition to the functional moiety, which is capable of being a hydrogen acceptor in a hydrogen bond. Without being bound to a theory the inventors believe that in the crystalline complexes of the present invention the phenyl ring has a pi-interaction with the thiophanate molecule. Preferably the phenyl ring is unsubstituted or carries 1, 2 or 3 radicals selected from halogen, $C_1$-$C_6$-alkoxy, $C_1$-$C_4$-haloalkyl, $C_1$-$C_4$-haloalkoxy, phenyl, which itself may be substituted or substituted by 1, 2, 3 or 4 radicals selected from $C_1$-$C_6$-alkyl, halogen, $C_1$-$C_6$-alkoxy, $C_1$-$C_4$-haloalkyl and $C_1$-$C_4$-haloalkoxy, and $C_1$-$C_6$-alkyl, which may be unsubstituted or substituted by one radical selected from alkoxy, cyano, phenyl, $C_1$-$C_4$-alkylcarbonyl, $C_1$-$C_4$-alkoxycarbonyl, carboxyl, carboxamido, $C_1$-$C_4$-alkylaminocarbonyl, $C_1$-$C_4$-dialkylaminocarbonyl and $C_1$-$C_4$-alkylcarbonylamino. Suitable radicals on the phenyl ring also include the following groups: $N(OCH_3)(C(O)OCH_3)$, $C(=CH—OCH_3)(C(O)OCH_3)$, $C(=CH—OCH_3)(C(O)NHCH_3)$, $C(=N—OCH_3)(C(O)OCH_3)$ and $C(=N—OCH_3)(C(O)OCH_3)$. Preference is given to unsubstituted phenyl or phenyl, which carries 1, 2 or 3 radicals selected from $C_1$-$C_6$-alkyl, halogen, $C_1$-$C_6$-alkoxy, $C_1$-$C_4$-haloalkyl and $C_1$-$C_4$-haloalkoxy, in particular from halogen and methyl, and phenyl which carries one of the following radicals:

$N(OCH_3)(C(O)OCH_3)$, $C(=CH—OCH_3)(C(O)OCH_3)$, $C(=CH—OCH_3)(C(O)NHCH_3)$, $C(=N—OCH_3)(C(O)OCH_3)$ or $C(=N—OCH_3)(C(O)OCH_3)$.

Preferably, the optionally substituted phenyl ring is linked to an unsubstituted or substituted aromatic nitrogen heterocycle that carries at least one imino nitrogen atom as ring member via a chemical bond or a 1- to 5-membered chain of atoms, preferably via a 2- or 3-membered chain of atoms. Generally the chain is formed by carbon atoms. However, one of the carbon atoms of the chain may be replaced by oxygen or silicon. The chain may be unsubstituted or carry 1, 2 or 3 substituents such cyano, OH, =O, $C_1$-$C_4$-alkyl, which may carry 1 or 2 radicals selected from OH, $C_1$-$C_2$-alkoxy, $C_1$-$C_2$-haloalkoxy, $C_1$-$C_2$-haloalkyl, trimethylsilyl, $C_3$-$C_6$-cycloalkyl and phenyl, which itself may carry 1, 2 or 3 radicals selected from halogen atoms and $C_1$-$C_4$-alkyl, or phenyl, which may carry 1, 2 or 3 radicals selected from halogen atoms and $C_1$-$C_4$-alkyl, or two radials that are bound to the same atom of the chain or to two adjacent atoms of the chain may form a 3 to 6 membered saturated carbocycle or heterocycle, which carries 1 or 2 oxygen atoms as ring members, the carbocycle and the heterocycle being unsubstituted or carrying a radical selected from halogen, $C_1$-$C_4$-alkyl, $C_1$-$C_4$-haloalkyl, $C_1$-$C_4$-alkoxy, halo-$C_1$-$C_4$-alkoxy and phenyl, which itself may carry 1, 2 or 3 radicals selected from halogen atoms and $C_1$-$C_4$-alkyl;

Suitable compounds A have a molecular weight, ranging from 150 to 500 Dalton.

Suitable compounds A may be selected from herbicide, fungicide and insecticides/acaricides. Example of suitable compounds A include:

Fungicides from the classes of
  Strobilurines, such as azoxystrobin, dimoxystrobin, enestroburin, fluoxastrobin, kresoxim-methyl, metominostrobin, picoxystrobin, pyraclostrobin, trifloxystrobin, orysastrobin, methyl(2-chloro-5-[1-(3-methyl-benzyloxyimino)-ethyl]-benzyl)-carbamate, methyl(2-chloro-5-[1-(6-methyl-pyridin-2-ylmethoxyimino)-ethyl]-benzyl)-carbamate, methyl 2-(ortho-(2,5-dimethylphenyl-oxymethylen)phenyl)-3-methoxyacrylate;

Anilides such as benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, 4-difluoromethyl-2-methyl-thiazol-5-[N-(4'-bromo-biphenyl-2-yl)]-carboxamid, 4-difluoromethyl-2-methyl-thiazol-5-[N-(4'-trifluoromethyl-biphenyl-2-yl)]-carboxamid, 4-difluoromethyl-2-methyl-thiazol-5-[N-(4'-chloro-3'-fluoro-biphenyl-2-yl)]-carboxamid, 3-difluoromethyl-1-methyl-pyrazol-4-[N-(3',4'-dichloro-4-fluoro-biphenyl-2-yl)]-carboxamid, 3-difluoromethyl-1-methyl-pyrazol-4-[N-(3',4'-di-chlor-5-fluor-biphenyl-2-yl)]-carboxamid, 3,4-dichloroisothiazol-5-[N-(2-cyano-phenyl)] carboxamid;

Morpholides such as dimethomorph, flumorph;

Benzoic acid amides such as flumetover, fluopicolide (picobenzamid), zoxamide;

Other carboxyamides, such as carpropamid, diclocymet, mandipropamid, N-(2-(4-[3-(4-Chlor-phenyl)-prop-2-inyloxy]-3-methoxy-phenyl)-ethyl)-2-methansulfonylamino-3-methyl-butyramid, N-(2-(4-[3-(4-Chlor-phenyl)-prop-2-inyloxy]-3-methoxy-phenyl)-ethyl)-2-ethansulfonylamino-3-methyl-butyramid;

Azole-fungicides, in particular:
  Triazoles: bitertanol, bromuconazole, cyproconazole, difenoconazole, diniconazole, enilconazole, epoxiconazole, fenbuconazole, flusilazole, fluquinconazole, flutriafol, hexaconazol, imibenconazole, ipconazole, metconazol, myclobutanil, penconazole, propiconazole, prothioconazole, simeconazole, tebuconazole, tetraconazole, triadimenol, triadimefon, triticonazole;
  imidazoles: cyazofamid, imazalil, pefurazoate, prochloraz, triflumizole;
  benzimidazole: benomyl, carbendazim, fuberidazole, thiabendazole;
  others: ethaboxam, etridiazole, mymexazole;
pyridines: fluazinam, pyrifenox, 3-[5-(4-chloro-phenyl)-2,3-dimethyl-isoxazolidin-3-yl]-pyridine;
pyrimidines: bupirimate, cyprodinil, ferimzone, fenarimol, mepanipyrim, nuarimol, pyrimethanil;
piperazines: triforine;
pyrroles: fludioxonil, fenpiclonil;
dicarboximides: Iprodione, procymidone, vinclozolin; and
other fungicidess: proquinazid, pyroquilon, quinoxyfen, tricyclazole, 5-chloro-7-(4-methyl-piperidin-1-yl)-6-(2,4,6-trifluorophenyl)-[1,2,4]triazolo[1,5-a]pyrimidine, 2-butoxy-6-iodo-3-propyl-chromen-4-on, 3-(3-bromo-6-fluoro-2-methylindol-1-sulfonyl)-[1,2,4] triazol-1-sulfonic acid dimethylamide and metrafenone.

Insecticide/Acaricide from the classes of:

Pyrethroids: acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cyphenothrin, cypermethrin, alpha-cypermethrin, beta-cypermethrin, theta-cypermethrin, zeta-cypermethrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, prallethrin, profluthrin, pyrethrin I thrin, permethrin, phenothrin, prallethrin, profluthrin, pyrethrin I and II, resmethrin, RU 15525, silafluofen, tau-fluvalinate, tefluthrin, tetramethrin, tralomethrin, transfluthrin, dimefluthrin, ZXI 8901;

Growth regulators: a) chitin synthesis inhibitors: benzoylureas; bistrifluron, chlorfluazuron, diflubenzuron, flucycloxuron, flufenoxuron, hexaflumuron, lufenuron, novaluron, noviflumuron, teflubenzuron, triflumuron; buprofezin, diofenolan, hexythiazox, etoxazole, clofentezine; b) ecdysone antagonists: chlormafenozide, halofenozide, methoxyfenozide, tebufenozide, azadirachtin; c) juvenoids: pyriproxyfen, hydroprene, kinoprene, methoprene, fenoxycarb; d) lipid biosynthesis inhibitors: spirodiclofen, spiromesifen, spirotetramat;

Nicotinic receptor agonists/antagonists compounds: acetamiprid, clothianidin, dinotefuran, imidacloprid, nitenpyram, thiacloprid, thiamethoxam, nicotine, bensultap, cartap hydrochloride, thiocyclam, thiosultap-sodium; the thiazol compound of formula ($I^1$)

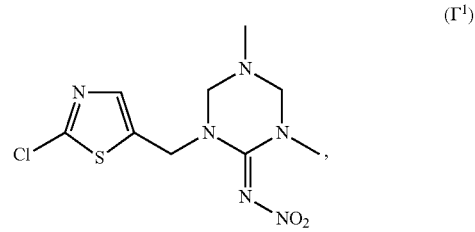 [SMILES: CN1CN(C)/C(=N\[N+](=O)[O-])N(Cc2cnc(Cl)s2)C1]

GABA antagonist compounds: acetoprole, ethiprole,), fipronil, vaniliprole, pyrafluprole, pyriprole, vaniliprole, Preferred compounds A include fungicides, selected from azoxystrobin, pyrachlostrobin, orysastrobin, epoxiconazol, tebuconazol, difenconazol, prothioconazol, prochloraz, triticonazol, fluquinconazol, metconazol, metalaxyl, mefenoxam and boscalid, and insecticides/acaricides selected from fipronil, acetamiprid, imidachloprid, thiamethoxam and clothianidin.

Particular preference is given to a crystalline complex, wherein the compound A is of the formula I

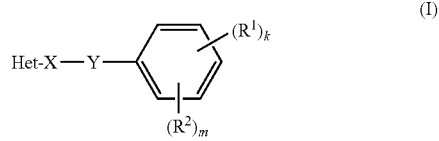

wherein

Het is imidazol-2-yl, pyrazol-1-yl, pyrazol-3-yl, 1,2,4-triazol-3-yl or 1,2,4-triazol-1-yl, in particular pyrazol-3-yl or 1,2,4-triazol-1-yl, wherein Het is unsubstituted or may carry 1 or 2 radicals selected from halogen atoms and $C_1$-$C_4$-alkyl and/or 1 phenyl group, which may carry 1, 2 or 3 halogen atoms;

X is O or a radical $CHR^3$;

Y is $CR^4R^5$ or $SiR^{4a}R^{5a}$, Y may also be O, if X is a a radical $CHR^3$; or X and Y together are a chemical bond or a bivalent radical of the formulae

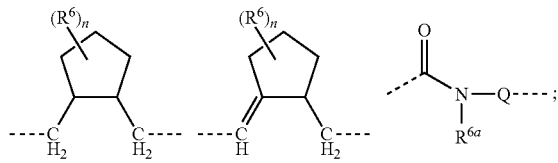

k is 0, 1 or 2;
m is 0 or 1;
n is 0, 1, 2 or 3;
$R^1$ is halogen, $C_1$-$C_4$-alkyl, methoxy, or phenyl;
$R^2$ selected from N(OCH$_3$)(C(O)OCH$_3$), C(=CH—OCH$_3$)(C(O)OCH$_3$), C(=CH—OCH$_3$)(C(O)NHCH$_3$), C(=N—OCH$_3$)(C(O)OCH$_3$) and C(=N—OCH$_3$)(C(O)OCH$_3$);
$R^3$ is hydrogen or $C_1$-$C_6$-alkyl, which may carry 1, 2, 3, 4 or 5 halogen atoms and/or 1 functional group selected from OH and a carbonyl group;
$R^4$ is hydrogen, CN, OH or $C_1$-$C_4$-alkyl or together with $R^3$ forms a bond;
$R^5$ is $C_1$-$C_4$-alkyl, which may carry 1 or 2 radicals selected from OH, $C_1$-$C_2$-alkoxy, $C_1$-$C_2$-haloalkoxy, trimethylsilyl, $C_3$-$C_6$-cycloalkyl and phenyl, which may carry 1, 2 or 3 radicals selected from halogen atoms and $C_1$-$C_4$-alkyl, or
  phenyl, which may carry 1, 2 or 3 radicals selected from halogen atoms and $C_1$-$C_4$-alkyl, or
$R^4$ and $R^5$ together form a 3 to 6 membered saturated heterocycle, which carries 1 or 2 oxygen atoms as ring members and which may carry a radical selected from halogen, $C_1$-$C_4$-alkyl, $C_1$-$C_4$-haloalkyl, $C_1$-$C_4$-alkoxy, halo-$C_1$-$C_4$-alkoxy and phenyl, which may carry 1, 2 or 3 radicals selected from halogen atoms and $C_1$-$C_4$-alkyl, in particular fluorine, chlorine or methyl;
$R^{4a}$ is $C_1$-$C_4$-alkyl or $C_1$-$C_4$-alkoxy, in particular methyl or methoxy;
$R^{5a}$ is $C_1$-$C_4$-alkyl, $C_1$-$C_4$-alkoxy or phenyl, which may carry 1, 2 or 3 radicals selected from halogen atoms and $C_1$-$C_4$-alkyl, in particular fluorine, chlorine or methyl;
$R^6$ is independently selected from OH and $C_1$-$C_4$-alkyl, in particular OH or methyl;
$R^{6a}$ is selected from hydrogen and $C_1$-$C_4$-alkyl, and
Q is $(CH_2)_p$ or $(CH_2)_qO$ with p being 1, 2, 3 or 4 and q being 1, 2 or 3.

Particular preferred compounds A include pyrachlostrobin, orysastrobin, epoxiconazol, prochloraz, triticonazol, fluquinconazol, metconazol, boscalid and fipronil.

Most preferred compounds A are selected from epoxiconazol, triticonazol, metconazol and pyrachlrostrobin.

A very preferred embodiment of the invention relates to a crystalline complex, wherein the compound A is epoxiconazol (IUPAC: (2RS,3SR)-1-[3-(2-chlorophenyl)-2,3-epoxy-2-(4-fluorophenyl)propyl]-1H-1,2,4-triazole).

Another very preferred embodiment of the invention relates to a crystalline complex, wherein the compound A is pyraclostrobin (IUPAC: methyl{2-[1-(4-chlorophenyl)-pyrazol-3-yloxymethyl]phenyl}(methoxy)carbamate).

Another very preferred embodiment of the invention relates to a crystalline complex, wherein the compound A is metconazole (IUPAC: (1RS,5RS;1RS,5SR)-5-(4-chlorobenzyl)-2,2-dimethyl-1-(1H-1,2,4-triazol-1-ylmethyl)cyclopentanol).

Another very preferred embodiment of the invention relates to a crystalline complex, wherein the compound A is tritconazole (IUPAC: (RS)-(E)-5-(4-chlorobenzylidene)-2,2-dimethyl-1-(1H-1,2,4-triazol-1-ylmethyl)cyclopentanol).

In the crystalline complexes according to the present invention, the molar ratio of thiophanate methyl and the compound A is at least 0.5:1 and may vary from 0.5:1 to 3:1 and is preferably from 0.8:1 to 2.5:1 or 0.9:1 to 2.1:1. In particular, the molar ratio is from 1:1 to 2:1, however, deviations are possible, though they will generally not exceed 20 mol-% and preferably 10%.

The crystalline complexes can be distinguished from simple mixtures of crystalline thiophanate methyl and crystalline compound A by standard analytical means used for the analysis of crystalline material, including X-ray powder diffractometry (PXRD), IR spectrometry, in particular the lack of narrow absorption bands at 3350 cm$^{-1}$ and 3305 cm$^{-1}$, characteristic for thiophanate methyl, solid state $^{13}$C-NMR ($^{13}$C-CP/MAS: cross polarization-magic angle spinning) and thermochemical analysis such as thermogravimetry (TGA) and differentials scanning calorimetry (DSC). Relative amounts of thiophanate methyl and compound A can be determined e.g. by HPLC or by $^1$H-NMR-spectroscopy.

For example, the crystalline complex of thiophanate methyl and epoxiconazol shows an X-ray powder diffractogram at 25° C. (Cu—Kα-radiation, 1.54178 Å) wherein the characteristic reflexes of the pure compounds are missing. In particular, the crystalline complex of thiophanate methyl and epoxiconazol shows at least 4, preferably at least 6, in particular at least 8 and more preferably all of the following reflexes, given in the following table 1 as 2θ values or as lattice spacings d:

TABLE 1

PXRD of the crystalline complex of thiophanate methyl and epoxiconazol

| 2θ values | d [nm] |
|---|---|
| 6.2 ± 0.2 | 14.31 ± 0.1 |
| 9.0 ± 0.2 | 9.85 ± 0.1 |
| 9.8 ± 0.2 | 8.98 ± 0.07 |
| 12.4 ± 0.2 | 7.13 ± 0.07 |
| 15.1 ± 0.2 | 5.88 ± 0.05 |
| 18.0 ± 0.2 | 4.92 ± 0.05 |
| 21.9 ± 0.2 | 4.05 ± 0.03 |
| 23.5 ± 0.2 | 3.78 ± 0.03 |
| 24.7 ± 0.2 | 3.61 ± 0.02 |
| 30.9 ± 0.2 | 2.89 ± 0.02 |

(25° C., Cu—Kα-radiation, 1.54178 Å)

In the crystalline complex according to said embodiment of the present invention, the molar ratio of thiophanate methyl and epoxiconazol is from 0.9:1 to 1.1:1 and in particular about 1:1.

Studies of single crystals of the crystalline complex of thiophanate methyl and epoxiconazol show that the basic crystal structure is triclinic and has the space group P-c. The structure analysis reveals that the crystalline complex is a 1:1 mixture of thiophanate methyl and epoxiconazol, the asymmetric cell containing one molecule of thiophanate methyl and epoxiconazol, each. In the crystal, two molecules of thiophanate methyl form a dimer through intermolecular hydrogen bonds in between the N—H and C=O groups of two adjacent thiophanate methyl molecules. The dimer appears to form two pockets which act as a receptor for two epoxiconazol molecules. It appears that there are hydrogen bonds between the nitrogen atoms of the triazole ring of the epoxiconazol molecule and the NH-groups of the thiophanate methyl molecules. Moreover, there seem to be a pi-interaction between the phenyl ring of the thiophanate methyl molecule and the fluorinated phenyl ring of the epoxiconazol molecule. This complex of two thiophanate methyl molecules and two epoxiconazol molecules forms a supramolecular synthon that is then packed in the crystal lattice to form the co-crystal. The characteristic data of the crystal structure of the complex are shown in table 2:

TABLE 2

Crystallographic data of the crystalline complex
of thiophanate methyl and epoxiconazol

| Parameter | |
|---|---|
| Class | Triclinic |
| Space group | P-1 |
| a | 982.7(3) pm |
| b | 1203.8(2) pm |
| c | 153.0(3) pm |
| α | 94.66(2)° |
| β | 108.57(2)° |
| γ | 111.00(2)° |
| Volume | 1.5618(5) nm³ |
| Z | 2 |
| Density (calculated) | 1.429 g/cm³ |
| R1, wR2 | 0.0436, 0.1233 | a, b, c = Length of the edges of the unit cell
α, β, γ = Angles of the unit cell
Z = Number of molecules in the unit cell Thermogravimetric analysis shows that the melting of the crystalline complex of epoxiconazol and thiophanate methyl starts at 148° C. followed by decomposition of thiophanate methyl.

For example, the crystalline complex of thiophanate methyl and pyraclostrobin shows an X-ray powder diffractogram at 25° C. (Cu—Kα-radiation, 1.54178 Å) wherein the characteristic reflexes of the pure compounds are missing. In particular, the crystalline complex of thiophanate methyl and pyraclostrobin shows in an X-ray powder diffractogram at 25° C. (Cu—Kα-radiation, 1.54178 Å) at least 4, preferably at least 6, in particular at least 8 and more preferably all of the following reflexes, given in the following table 3 as 2θ values or as lattice spacings d.

TABLE 3

PXRD of the crystalline complex of thiophanate
methyl and pyraclostrobin

| 2θ values | d [nm] |
|---|---|
| 4.9 ± 0.2 | 18.00 ± 0.1 |
| 6.8 ± 0.2 | 13.03 ± 0.1 |
| 8.5 ± 0.2 | 10.47 ± 0.1 |
| 12.0 ± 0.2 | 7.36 ± 0.07 |
| 14.5 ± 0.2 | 6.10 ± 0.05 |
| 16.9 ± 0.2 | 5.24 ± 0.05 |
| 20.4 ± 0.2 | 4.36 ± 0.03 |
| 22.9 ± 0.2 | 3.89 ± 0.03 |
| 25.5 ± 0.2 | 3.50 ± 0.02 |
| 29.3 ± 0.2 | 3.05 ± 0.02 |

(25° C., Cu—Kα-radiation, 1.54178 Å)

$^{13}$C-CP/MAS confirms the presence of a crystalline complex rather than the presence of a simple mixture of solid thiophanate methyl and solid pyraclostrobin. In particular, the $^{13}$C-CP/MAS of the crystalline complexes (CP=3 ms, D1=30 s, 25° C., RO 5700 Hz). shows chemical shifts at δ 182.0, 180.8, 178.7; 177.7, 164.3, 158.8, 154.9, 154.0, 152.1 139.4, 137.9, 134.3, 131.2, 130.2, 127.6, 125.9, 123.8, 117.7, 115.6, 94.3, 65.7, 63.0, 58.8, 54.3, 53.6 and 52.6. The shifts 164.3, 158.8 ppm are most characteristic and lack in the $^{13}$C-CP/MAS of thiophanate methyl and pyraclostrobin. Polarisation transfer experiments from the protons to $^{13}$C confirm that thiophanate methyl and pyraclostrobin are present as a co-crystal and not as a mixture of crystalline material of the pure compounds.

In the crystalline complex according to said embodiment of the present invention, the molar ratio of thiophanate methyl and pyraclostrobin may vary from 1.1:1 to 2.5:1, and is in particular from 1.9:1 to 2.1:1, especially about 2:1.

Thermogravimetric analysis shows that the melting point of the crystalline complex of pyraclostrobin and thiophanate methyl is about 150° C.

For example, the crystalline complex of thiophanate methyl and metconazol shows an X-ray powder diffractogram at 25° C. (Cu—Kα-radiation, 1.54178 Å) wherein the characteristic reflexes of the pure compounds are missing. In particular, the crystalline complex of thiophanate methyl and epoxiconazol shows at least 4, preferably at least 6, in particular at least 8 and more preferably all of the following reflexes, given in the following table 4 as 2θ values or as lattice spacings d:

TABLE 4

PXRD of the crystalline complex of
thiophanate methyl and metconazol

| 2θ values | d [nm] |
|---|---|
| 5.0 ± 0.2 | 17.96 ± 0.1 |
| 9.9 ± 0.2 | 8.94 ± 0.08 |
| 11.3 ± 0.2 | 7.83 ± 0.03 |
| 12.0 ± 0.2 | 7.39 ± 0.02 |
| 15.0 ± 0.2 | 5.92 ± 0.01 |
| 16.7 ± 0.2 | 5.32 ± 0.01 |
| 18.1 ± 0.2 | 4.91 ± 0.01 |
| 21.6 ± 0.2 | 4.10 ± 0.01 |
| 27.8 ± 0.2 | 3.21 ± 0.01 |

(25° C., Cu—Kα-radiation, 1.54178 Å)

In the crystalline complex according to said embodiment of the present invention, the molar ratio of thiophanate methyl and metconazol is from 0.9:1 to 1.1:1 and in particular about 1:1.

Studies of single crystals of the crystalline complex of thiophanate methyl and metconazol show that the basic crystal structure is monoclinic and has the space group P2(1)/c. The structure analysis reveals that the crystalline complex is a 1:1 mixture of thiophanate methyl and metconazol, the asymmetric cell containing one molecule of thiophanate methyl and metconazol, each. It appears that there are hydrogen bonds between the nitrogen atoms of the triazole ring of the metconazol molecule and the NH-groups of the thiophanate methyl molecules. The characteristic data of the crystal structure of the complex are shown in table 5:

TABLE 5

Crystallographic data of the crystalline complex
of thiophanate methyl and metconazol

| Parameter | |
|---|---|
| Class | Monoclinic |
| Space group | P2(1)/c |
| a | 178.97(3) pm |
| b | 105.88(2) pm |
| c | 168.77(3) pm |
| α | 90° |
| β | 94.363(5)° |
| γ | 90° |
| Volume | 3.1889(5) nm³ |
| Z | 4 |
| Density (calculated) | 1.379 g/cm³ |
| R1, wR2 | 0.049, 0.153 |

(−170° C.)
a, b, c = Length of the edges of the unit cell
α, β, γ = Angles of the unit cell
Z = Number of molecules in the unit cell The DSC-measurement of the crystalline complex of metconazole and thiophanate methyl shows an endothermic melting peak with onset at 155 to 158° C. and peak maximum at 160-168° C. This is about 60 degrees higher than the pure crystalline metconazole (100° C., as reported in Pesticide Manual) and about 10 to 20° C. lower than the melting point of thiophanate-methyl.

The crystalline complexes of the present invention can be prepared by co-crystallizing thiophanate-methyl and at least one compound A from a solution or slurry or from a melt containing thiophanate-methyl and at least one compound A. Likewise, it is possible to prepare the crystalline complexes of the present invention, by grinding a mixture of the compound A and thiophanate methyl at elevated temperature, e.g. above 30° C., preferably at a temperature of at least 40° C., in particular of at least 50° C., more preferably of at least 55° C., e.g. from >30° C. to 110° C., preferably from 40° C. to 100° C., in particular from 50° C. to 90° C. or from 55° C. to 90° C. The compound A may be solid at the grinding temperature. However, this is not necessary and it might be advantageous if the temperature is close to or above the melting point of the compound A.

In a preferred embodiment the crystalline complex is thiophanate-methyl and at least one compound A is obtained from a slurry of thiophanate-methyl and the at least one compound A in an organic solvent or in a mixture of water and organic solvent. Consequently, this method comprises suspending thiophanate-methyl and the active compound A in an organic solvent or in a mixture of water and an organic solvent (Slurry process).

Preferred organic solvents for the slurry process are those, which are at least partially water miscible, i.e. which have miscibility with water of at least 10% v/v, more preferably at least 20% v/v at room temperature, mixtures thereof and mixtures of said water miscible solvents with organic solvents that have miscibility with water of less than 10% v/v at room temperature. Preferably the organic solvent comprises at least 80% v/v, based on the total amount of organic solvent, of the at least one water miscible solvent.

Suitable solvents having a water miscibility of at least 10% at room temperature include, but are not limited to:
1. $C_1$-$C_4$-Alkanols such as methanol, ethanol, n-propanol or isopropanol;
2. Amides, N-methylamides and N,N-dimethylamides of $C_1$-$C_3$-carboxylic acids such as formamide, dimethylformamide (DMF), acetamide and N,N-dimethylacetamide;
3. 5 or 6-membered lactames with a total of 7 carbon atoms such as pyrrolidone, N-methylpyrrolidone, N-ethylpyrrolidone, N-isopropylpyrrolidone, N-hydroxyethylpyrrolidone;
4. Dimethylsulfoxid and sulfolane;
5. Ketones with 3 to 6 carbon atoms such as acetone, 2-butanone, cyclopentanone and cyclohexanone;
6. Acetonitrile;
7. 5- or 6-membered lactones such as γ-butyrolactone;
8. Polyols and polyetherols such as glycol, glycerin, dimethoxyethan, ethylendiglycol, ethylenglycolmonomethylether, etc;
9. Cyclic carbonates having 3 to 5 carbon atoms including propylene carbonate and ethylene carbonate; and
10. Cyclic ethers such as tetrahydrofurane, dioxane and trioxane, dimethyl(poly)$C_2$-$C_3$-alkyleneglycol ethers such as dimethoxyethane, diethyleneglycoldimethylether, triethyleneglycoldimethylether, dipropyleneglycoldimethylether, low molecular weight polyethyleneglycoles and low molecular weight polypropyleneglycoles (MW≤400).

More preference is given to organic solvents of the groups 1, 6, 8 and 9, and to their mixtures with water. In the mixtures with water the relative amount of organic solvent and water may vary from 10:1 to 1:10, in particular from 2:1 to 1:5.

The slurry process can by simply performed by suspending thiophanate methyl and the at least one compound A in the organic solvent or solvent/water mixture. The relative amounts of thiophanate methyl, the at least one compound A and solvent or solvent/water mixture will be chosen to obtain a suspension at the given temperature. Complete dissolution of thiophanate methyl and the at least one compound A should be avoided. In particular thiophanate methyl and the at least one compound A are suspended in an amount from 50 to 800 g, more preferably 100 to 600 g per liter of solvent or solvent/water mixture.

The relative molar amount of thiophanate methyl and the at least one compound A may vary from 1:2 to 20:1, preferably from 1:1 to 15:1. If one of the components is in excess with regard to the stoichiometry of the crystalline complex, a mixture of the crystalline complex and the compound being in excess might be obtained, though a minor excess might remain dissolved in the mother liquor. For formulation purposes, the presence of an excess of compound A or thiophanate methyl might be acceptable. In particular the presence of an excess of thiophanate methyl does not cause stability problems. For preparing the pure crystalline complex, thiophanate methyl and compound A will be used in a relative molar amount which is close to the stoichiometry of the complex to be formed and which usually will not deviate more than 50 mol.-%, based on the stoichiometrically required amount.

The slurry process is usually performed at a temperature of at least 10° C., preferably at least 20° C. and in particular at least 30° C., e.g. from 20 to 90° C., preferably from 30 to 85° C., in particular from 40 to 70° C.

The time required for formation of the crystalline complex by the slurry process depends on the temperature, the type of solvent and is generally at least 12 h. In any case, complete conversion is achieved after one week, however, the complete conversion will usually require not more than 24 h.

In another preferred embodiment of the invention the crystalline complex is prepared by applying shear forces to a liquid which contains suspended particles of thiophanatemethyl and active compound A at a temperature of at least 30° C. until the crystalline complex has been formed (shear process).

In the liquid, thiophanate methyl and the at least one compound A are present as particles, which are suspended in a liquid medium. Upon applying shear forces to the liquid at elevated temperatures the formation of the crystalline complex takes place.

The main constituent of the liquid medium is water or an organic solvent, in which thiophanate methyl and the compound A is practically insoluble, i.e. the solubility at 25° C. is less than 5 g/l, in particular less than 1 g/l. Suitable organic solvents include aliphatic hydrocarbons, mineral spirits, plant oils and plant oil esters. In a preferred embodiment, the liquid medium contains water or a mixture of water with up to 20% v/v of a water miscible solvent, in particular a solvent of the group 1. or 9, as main constituent. Apart from that, the liquid medium may also contain additives which are usually present in a liquid suspension concentrates.

The liquid medium may contain thiophanate methyl and the crystalline compound A in an amount from 5 to 70% by weight, in particular from 10 to 60% by weight and more preferably from 15 to 50% by weight, based on the total weight of the liquid medium, the compound A and thiophanate methyl.

The liquid medium may contain thiophanate methyl and the crystalline compound A in a relative molar amount of thiophanate methyl and the at least one compound A varying from 1:2 to 20:1, preferably from 1:1 to 15:1. If one of the components is in excess with regard to the stoichiometry of the crystalline complex, a mixture of the crystalline complex and the compound being in excess will be obtained. For formulation purposes, the presence of an excess of compound A or thiophanate methyl might be acceptable. In particular the presence of an excess of thiophanate methyl does not cause stability problems. Likewise, the presence of an excess of compound A does usually not cause stability problems. However, it is preferred, that a formulation does not contain both uncomplexed thiophanate methyl and uncomplexed compound A in amounts of more than 20% by weight each, nor in particular in amounts of more than 10% by weight each, based on the amount of compound A and thiophanate present in the form of the crystalline complex, in order to avoid uncontrolled formation of the complex in the formulation. Therefore, the present invention relates in particular to formulations containing the crystalline complex of the present invention, provided that, if both compounds A and thiophanate are present in the formulation in non-complexed form, the amount of the compound A does not exceed 20% by weight, in particular 10% by weight, based on the amount of complex in the formulation, and at the same time, the amount of thiophanate methyl does not exceed 20% by weight, in particular 10% by weight, based on the amount of complex in the formulation.

The liquid medium may include additives which are usually present in a liquid suspension concentrate. Suitable additives are described hereinafter and include surfactants, in particular anionic or non-ionic emulsifiers, wetting agents and dispersants usually employed in crop protection compositions, furthermore antifoam agents, antifreeze agents, agents for adjusting the pH, stabilizers, anticaking agents, dyes and biocides (preservatives). Preferably, the liquid medium does not contain viscosity-modifying additives (thickeners). The amount of surfactants will generally be from 0.5 to 20% by weight, in particular from 1 to 15% by weight and particularly preferably from 1 to 10% by weight, based on the total weight of the liquid medium, the compound A and thiophanate methyl. The amount of anti-freeze agents may be up to 10% by weight, in particular up to 20% by weight, e.g. from 0.5 to 20% by weight, in particular from 1 to 10% by weight, based on the total weight of the liquid medium, the compound A and thiophanate methyl. Further additives, apart from anti-freeze agents and surfactants, may be present in amounts from 0 to 5% by weight, based on the total weight of the liquid medium, the compound A and thiophanate methyl.

The temperature required for formation of the crystalline complex is generally at least 30° C., preferably at least 35° C. and in particular at least 40° C., more preferably at least 50° C., especially at least 55° C., e.g. from 30 to 100° C., preferably from 35 to 100° C., in particular from 40 to 100° C., more preferably from 50 to 90° C. and especially from 55 to 80° C.

The time required for formation of the crystalline complex depends in a manner known per se on the type of shear process and the temperature and can be determined by the person skilled in the art in standard experiments. Shearing times in the range of e.g. from 30 min. to 48 hours have been found to be suitable, although a longer period of time is also conceivable. A shearing time of 1 to 24 hours is preferred.

Shear forces can be applied by suitable techniques, which are capable of providing sufficient shear to bring the particles of thiophanate methyl and the at least one compound A into an intimate contact. Suitable techniques include grinding, crushing or milling, in particular by wet grinding or wet milling, including e.g. bead milling or by use of a colloid mill. Suitable shearing devices include in particular ball mills or bead mills, agitator ball mills, circulating mills (agitator ball mills with pin grinding system), disk mills, annular chamber mills, double cone mills, triple roll mills, batch mills, colloid mills, and media mills, such as sand mills. To dissipate the heat energy introduced during the grinding process, the grinding chambers are preferably fitted with cooling systems. Particularly suitable is the ball mill Drais Superflow DCP SF 12 from DRAISWERKE, INC. 40 Whitney Road. Mahwah, N.J. 07430 USA, a Drais Peri Mill PMC from DRAISWERKE, INC., the circulating mill system ZETA from Netzsch-Feinmahltechnik GmbH, the disk mill from Netzsch Feinmahltechnik GmbH, Selb, Germany, the bead mill Eiger Mini 50 from Eiger Machinery, Inc., 888 East Belvidere Rd., Grayslake, Ill. 60030 USA and the bead mill DYNO-Mill KDL from WA Bachofen AG, Switzerland. However, other homogenizers might also be suitable, including high shear stirrers, Ultra-Turrax apparatus, static mixers, e.g. systems having mixing nozzles and other homogenizers such as colloid mills.

In a preferred embodiment of the invention, shear is applied by bead milling. In particular, bead sizes in the range of from 0.05 to 5 mm, more particularly from 0.2 to 2.5 mm, and most particularly from 0.5 to 1.5 mm have been found to be suitable. In general, bead loadings in the range of from 40 to 99%, particularly from 70 to 97%, and more particularly from 65 to 95% may be used.

After having applied sufficient shear forces a suspension of the crystalline complex, optionally in admixture with excess thiophanate methyl or active compound A, is obtained, wherein 90% by weight of the suspended particles have the particle size of not more than 30 μm, preferably not more than 20 μm, in particular not more than 10 μm especially not more than 5 μm, as determined by dynamic light scattering.

The thus obtained liquid suspension of the crystalline complex can, after, or in particular before a formulation with additives, be converted by customary drying methods, in particular by spray-drying or freeze-drying, into powder compositions. Before or during drying, a drying or spray auxiliary may be added. Suitable drying or spray auxiliaries for drying aqueous dispersions are known. These include protective colloids, such as polyvinyl alcohol, in particular polyvinyl alcohol having a degree of hydrolysis of >70%, carboxylated polyvinyl alcohol, phenolsulfonic acid/formaldehyde condensates, phenolsulfonic acid/urea/formaldehyde condensates, naphthalenesulfonic acid/formaldehyde condensates, naphthalenesulfonic acid/formaldehyde/urea condensates, polyvinylpyrrolidone, copolymers of maleic acid (or maleic anhydride) and vinylaromatics such as styrene and ethoxylated derivatives thereof, copolymers of maleic acid or maleic anhydride with $C_2$-$C_{10}$-olefins, such as diisobutene, and ethoxylated derivatives thereof, cationic polymers, for example homo- and copolymers of N-alkyl-N-vinylimidazolinium compounds with N-vinyl lactams and the like, and also inorganic anti-blocking agents (sometimes also termed as anti-caking agents), such as silicic acid, in particular pyrogenic silica, alumina, calcium carbonate and the like. The drying auxiliaries are usually employed in an amount of from 0.1 to 20% by weight, based on the weight of the active compound particles in the liquid pesticide composition of the present invention.

As already mentioned above, the crystalline complex as defined herein are suitable for preparing crop protection compositions and in particular for preparing aqueous suspension concentrates. Accordingly, the invention also provides a composition for crop protection, comprising a crystalline complex as defined herein, if appropriate a liquid phase and also, if appropriate, customary, generally solid carriers and/or auxiliaries. Suitable carriers are, in principle, all solid substances usually used in crop protection compositions, in particular in fungicides. Solid carriers are, for example, mineral earths, such as silica gels, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

In the case of liquid formulations of the crystalline complexes, the compositions have a liquid phase. Suitable liquid phases are, in principle, water and also organic solvents in which pyraclostrobin has low or no solubility, for example those in which the solubility of pyraclostrobin at 25° C. and 1013 mbar is not more than 1% by weight, in particular not more than 0.1% by weight and especially not more than 0.01% by weight.

Typical auxiliaries comprise surfactants, in particular the wetting agents and dispersants usually employed in crop protection compositions, furthermore viscosity-modifying additives (thickeners), antifoam agents, antifreeze agents, agents for adjusting the pH, stabilizers, anticaking agents and biocides (preservatives).

The invention relates in particular to compositions for crop protection in the form of suspension concentrate, in particular an aqueous suspension concentrate (SC). Such suspension concentrates comprise the crystalline complex in a finely divided particulate form, where the particles of the crystalline complex are suspended in an liquid medium, preferably in an aqueous medium. The size of the active compound particles, i.e. the size which is not exceeded by 90% by weight of the active compound particles, is typically not more than 30 µm, preferably not more than 20 µm, in particular not more than 10 µm, especially not more than 5 µm, as determined by dynamic light scattering. Advantageously, at least 40% by weight and in particular at least 60% by weight of the particles in the SCs according to the invention have diameters below 2 µm.

Suspension concentrates, in particular aqueous suspension concentrates can be prepared by suspending the crystalline complex in a suitable liquid carrier, which may contain conventional formulation additives as described hereinafter. However, it is preferred to prepare the suspension concentrate by the shear process as described herein, i.e. by applying shear forces to a liquid which contains suspended particles of thiophanate-methyl and active compound A and optionally further additives at a temperature of at least 30° C. until the crystalline complex has been formed.

In addition to the active compound, suspension concentrates typically comprise surfactants, and also, if appropriate, antifoam agents, thickeners, antifreeze agents, stabilizers (biocides), agents for adjusting the pH and anticaking agents.

In such SCs, the amount of active compound, i.e. the total amount of the crystalline complex and, if appropriate, further active compounds is usually in the range from 10 to 70% by weight, in particular in the range from 15 to 50% by weight, based on the total weight of the suspension concentrate.

Preferred surfactants are anionic and non-ionic surfactants (emulsifiers). Suitable surfactants are also protective colloids. The amount of surfactants will generally be from 0.5 to 20% by weight, in particular from 1 to 15% by weight and particularly preferably from 1 to 10% by weight, based on the total weight of the SCs according to the invention. Preferably, the surfactants comprise at least one anionic surfactant and at least one non-ionic surfactant, the ratio of anionic to non-ionic surfactant typically being in the range from 10:1 to 1:10.

Examples of anionic surfactants (anionic tensides, emulsifiers and dispersants) include alkylaryl sulfonates, phenyl sulfonates, alkyl sulfates, alkyl sulfonates, alkyl ether sulfates, alkylaryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, alkyl phosphates, alkylaryl phosphates, for example tristyryl phosphates, and the alkali metal, alkaline earth metal, ammonium and amine salts of the substances mentioned above. Preferred anionic surfactants are those which carry at least one sulfonate group, and in particular their alkali metal and their ammonium salts.

Examples of non-ionic surfactants (non-ionic emulsifiers and dispersants) comprise alkylphenol alkoxylates, alcohol alkoxylates, fatty amine alkoxylates, polyoxyethylene glycerol fatty acid esters, castor oil alkoxylates, fatty acid alkoxylates, fatty amide alkoxylates, fatty polydiethanolamides, lanolin ethoxylates, fatty acid polyglycol esters, isotridecyl alcohol, fatty amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and mixtures thereof. Preferred non-ionic surfactants are fatty alcohol ethoxylates, alkyl polyglycosides, glycerol fatty acid esters, castor oil alkoxylates, fatty acid alkoxylates, fatty amide alkoxylates, lanolin ethoxylates, fatty acid polyglycol esters and ethylene oxide/propylene oxide block copolymers and mixtures thereof.

Protective colloids are typically water soluble, amphiphilic polymers. Examples include proteins and denatured proteins such as casein, polysaccharides such as water soluble starch derivatives and cellulose derivatives, in particular hydrophobic modified starches and celluloses, furthermore polycarboxylates such as polyacrylic acid (polyacrylates), acrylic acid or methacrylic acid copolymers or maleic acid copolymers such as acrylic acid/olefin copolymers, acrylic acid, styrene copolymers, maleic anhydride/olefin copolymers (for example Sokalan® CP9, BASF) and the esterification products of said copolymers with polyethylene glycols, polyvinylalcohol, polyvinylpyrrolidone, vinylpyrrolidone copolymers, polyvinylamines, polyethylenimines and polyalkylene ethers.

In particular, the SCs according to the invention comprise at least one surfactant which improves wetting of the plant parts by the aqueous application form (wetting agent) and at least one surfactant which stabilizes the dispersion of the active compound particles in the SC (dispersant). The amount of wetting agent is typically in the range from 0.5 to 10% by weight, in particular from 0.5 to 5% by weight and especially from 0.5 to 3% by weight, based on the total weight of the SC. The amount of dispersant is typically from 0.5 to 10% by weight and in particular from 0.5 to 5% by weight, based on the total weight of the SC.

Preferred wetting agents are of anionic or non-ionic nature and selected, for example, from naphthalenesulfonic acids including their alkali metal, alkaline earth metal, ammonium and amine salts, furthermore fatty alcohol ethoxylates, alkyl polyglycosides, glycerol fatty acid esters, castor oil alkoxylates, fatty acid alkoxylates, fatty amide alkoxylates, fatty polydiethanolamides, lanolin ethoxylates and fatty acid polyglycol esters.

Preferred dispersants are of anionic or non-ionic nature and selected, for example, from polyethylene glycol/polypropylene glycol block copolymers, polyethylene glycol alkyl ethers, polypropylene glycol alkyl ethers, polyethylene glycol/polypropylene glycol ether block copolymers, alkylaryl phosphates, for example tristyryl phosphates, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, polycarboxylates, such as, for example, polyacrylates, maleic anhydride/olefin copolymers (for example Sokalan® CP9, BASF), including the alkali metal, alkaline earth metal, ammonium and amine salts of the substances mentioned above.

Viscosity-modifying additives (thickeners) suitable for the SCs according to the invention are in particular compounds which bestow upon the formulation pseudoplastic flow properties, i.e. high viscosity in the resting state and low viscosity in the agitated state. Suitable are, in principle, all compounds used for this purpose in suspension concentrates. Mention may be made, for example, of inorganic substances, such as bentonites or attapulgites (for example Attaclay® from Engelhardt), and organic substances, such as polysaccharides and heteropolysaccharides, such as Xanthan Gum® (Kelzan® from Kelco), Rhodopol® 23 (Rhone Poulenc) or Veegum® (from R.T. Vanderbilt), and preference is given to using Xanthan-Gum®. Frequently, the amount of viscosity-modifying additives is from 0.1 to 5% by weight, based on the total weight of the SC.

Antifoam agents suitable for the SCs according to the invention are, for example, silicone emulsions known for this purpose (Silikon® SRE, from Wacker, or Rhodorsil® from Rhodia), long-chain alcohols, fatty acids, defoamers of the type of aqueous wax dispersions, solid defoamers (so-called compounds), organofluorine compounds and mixtures thereof. The amount of antifoam agent is typically from 0.1 to 1% by weight, based on the total weight of the SC.

Preservatives may be added for stabilizing the suspension concentrates according to the invention. Suitable preservatives are those based on isothiazolones, for example Proxel® from ICI or Acticide® RS from Thor Chemie or Kathon® MK from Rohm & Haas. The amount of bactericides is typically from 0.05 to 0.5% by weight, based on the total weight of the SC.

Suitable antifreeze agents are liquid polyols, for example ethylene glycol, propylene glycol or glycerol. The amount of antifreeze agents is generally from 1 to 20% by weight, in particular from 5 to 10% by weight, based on the total weight of the suspension concentrate.

If appropriate, the SCs according to the invention may comprise buffers for regulating the pH. Examples of buffers are alkali metal salts of weak inorganic or organic acids, such as, for example, phosphoric acid, boric acid, acetic acid, propionic acid, citric acid, fumaric acid, tartaric acid, oxalic acid and succinic acid.

If the formulations of the crystalline complexes are used for seed treatment, they may comprise further customary components as employed in the seed treatment, e.g. in dressing or coating. Examples are in particular colorants, stickers, fillers, and plasticizers besides the above-mentioned components.

Colorants are all dyes and pigments which are customary for such purposes. In this context, both pigments, which are sparingly soluble in water, and dyes, which are soluble in water, may be used. Examples which may be mentioned are the dyes and pigments known under the names Rhodamin B, C. I. Pigment Red 112 and C. I. Solvent Red 1, Pigment blue 15:4, Pigment blue 15:3, Pigment blue 15:2, Pigment blue 15:1, Pigment blue 80, Pigment yellow 1, Pigment yellow 13, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108. The amount of colorants will usually not exceed 20% by weight of the formulation and preferably ranges from 0.1 to 15% by weight, based on the total weight of the formulation.

Stickers are all customary binders which can be employed in dressing products. Examples of suitable binders comprise thermoplastic polymers such as polyvinylpyrrolidone, polyvinyl acetate, polyvinyl alcohol and tylose, furthermore polyacrylates, polymethacrylates, polybutenes, polyisobutenes, polystyrene, polyethylenamines, polyethylenamides, the aforementioned protective colloids, polyesters, polyetheresters, polyanhydrides, polyesterurethanes, polyesteramides, thermoplastic polysaccharides, e.g. cellulose derivates such as celluloseesters, celluloseethers, celluloseetheresters including methylcellulose, ethylcellullose, hydroxymethylcellulose, carboxymethylcellulose, hydroxypropylcellulose and starch derivatives and modified starches, dextrines, maltodextrines, alginates and chitosanes, moreover fats, oils, proteins, including casein, gelatin and zeins, gum arabics, shellacs. Preferred stickers are biocompatible, i.e. they do not have a noticable phytotoxic activity. Preferably the stickers are biodegradable. Preferably the sticker is chosen that it acts as a matrix for the active ingredients of the formulation. The amount of stickers will usually not exceed 40% by weight of the formulation and preferably ranges from 1 to 40% by weight, and in particular in the range from 5 to 30% by weight, based on the total weight of the formulation.

Besides the sticker the formulation may also contain inert fillers. Examples for these include the aforementioned solid carrier materials, especially fine particulate inorganic materials such as clays, chalk, bentonite, caolin, talc, perlite, mica, silica, diatomaceaous earth, quartz powder, montmorillonite, but also fine particulate organic materials such as wood flours, cereal flours, activated carbon and the like. The amount of filler is preferably chosen that the total amount of filler does not exceed 75% by weight, based on the total weight of all non-volatile components of the formulation. Commonly, the amount of filler ranges from 1 to 50% by weight, based on the total weight of all non-volatile components of the formulation.

Besides, the formulation may also contain a plasticizer, which increases the flexibility of the coating. Examples of plasticizers include oligomeric polyalkylenglycoles, glycerol, dialkyl phthalates, alkylbenzyl phthalates, glycol benzoates and related compounds. The amount of plasticizer in the coating frequently ranges from 0.1 to 20% by weight, based on the total weight of the formulation.

The crystalline complexes of the invention can be used in a manner known per se for controlling phytopathogenic fungi or insect pests, depending on the compound A. In particular, the crystalline complexes can be formulated together with further active compounds, to increase the activity and/or to widen the activity, spectrum. These include, in principle, all insecticides and fungicides which are typically used together with pyraclostrobin. The novel crystalline complexes of the invention may be used in plant protection as foliar, dressing and soil fungicides.

They are particularly important for combating a multitude of fungi on various cultivated plants, such as wheat, rye, barley, triticale, oats, rice, corn, grass, bananas, cotton, soya, coffee, sugar cane, vines, fruits and ornamental plants, and vegetables, such as cucumbers, beans, tomatoes, potatoes and cucurbits, and on the seeds of these plants.

The crystalline complexes of the invention are particularly suitable for the joint formulation as suspension concentrates with active compounds which for their part can be formulated as suspension concentrates. Accordingly, a preferred embodiment of the invention relates to suspension concentrates which, in addition to the crystalline complex, comprise at least one further active compound in finely divided, particulate form. With respect to particle sizes, amount of active compound and auxiliaries, what was said above applies.

Typical further mixing partners of the crystalline complexes include the aforementioned compounds A, in particular the aforementioned fungicides and insecticides/acaricides.

In principle, the formulations of the crystalline complexes according to the present invention can be used for combating all plant diseases caused by harmful fungi or other pests, which can be combated with conventional formulations of a combination of the thiophanate methyl and the active compound A. Depending on the compound A or the further mixing partner, for example, it is one of the following plant diseases:

*Alternaria* species on vegetables, rapeseed, sugar beet, soya, cereals, cotton, fruit and rice,
  (e.g. *A. solani* or *A. alternata* on potatoes and various plants)
*Aphanomyces* species on sugar beet and vegetables,
*Ascochyta* sp. on cotton and rice,
*Bipolaris* and *Drechslera* species on corn, cereals, rice and lawns,
  (e.g. *D. teres* on barley, *D. tritci-repentis* an wheat)
*Blumeria graminis* (powdery mildew) on cereals,
*Botrytis cinerea* (gray mold) on strawberries, vegetables, flowers and grapevines,
*Botryodiplodia* sp. on cotton,
*Bremia lactucae* on lettuce,
*Cercospora* species on corn, soybeans, rice and sugar beet,
  (e.g. *C. beticula* on sugar beets),
*Cochliobolus* species on corn, cereals, rice (e.g. *Cochliobolus sativus* on cereals, *Cochliobolus miyabeanus* on rice),
*Corynespora* sp. on soybeans, cotton and various plants,
*Colletotricum* species on soybean, cotton, and various plants,
  (e.g. *C. acutatum* on various plants)
*Curvularia* sp. on cereals and rice,
*Diplodia* sp. on cereals and corn,
*Exserohilum* species on corn,
*Erysiphe cichoracearum* and *Sphaerotheca fuliginea* on cucurbits,
*Fusarium* and *Verticillium* species (e.g. *V dahliae*) on various plants, (e.g. *F. graminearum* on wheat)
*Gaeumanomyces graminis* on cereals,
*Gibberella* species on cereals and rice (e.g., *Gibberella fujikuroi* on rice),
*Grainstaining complex* on rice,
*Helminthosporium* species (e.g. *H. graminicola*) on corn and rice,
*Macrophomina* sp. on soya and cotton,
*Michrodochium* sp, e. g. *M. nivale*, on cereals,
*Mycosphaerella* species on cereals, bananas and peanuts, (*M. graminicola* on wheat, *M. fijiesis* on bananas),
*Phaeoisaripsis* sp. on soybeans
*Phakopsara* sp, e.g. *P. pachyrhizi* and *Phakopsara meibomiae* on soybeans,
*Phoma* sp. on soybeans
*Phomopsis* species on soybeans, sunflowers and grapevines, (*P. viticola* on grapevines, *P. helianthii* sunflowers),
*Phytophthora infestans* on potatoes and tomatoes,
*Plasmopara viticola* on grapevines,
*Penecilium* sp. on soybeans and cotton,
*Podosphaera leucotricha* on apples,
*Pseudocercosporella herpotrichoides* on cereals,
*Pseudoperonospora* species on hops and cucurbits, (e.g. *P. cubenis* on cucumber),
*Puccinia* species on cereals, corn and aspargus (*P. triticina* and *P. striformis* on wheat, *P. asparagi* on asparagus),
*Pyrenophora* species on cereals,
*Pyricularia oryzae, Corticium sasakii, Sarocladium oryzae, S. attenuatum, Entyloma oryzae* on rice,
*Pyriculana grisea* on lawns and cereals,
*Pythium* spp. on lawns, rice, corn, cotton, rapeseed, sunflowers, sugar beet, vegetables and various plants,
*Rhizoctonia* species (e.g. *R. solani*) on cotton, rice, potatoes, lawns, corn, rapeseed, potatoes, sugar beet, vegetables and various plants,
*Rynchosporium* sp. (e.g. *R secali*) on rice and cereals,
*Sclerotinia* species on rapeseed, sunflowers, and various plants,
*Septoria tritici* and *Stagonospora nodorum* on wheat,
*Erysiphe* (syn. *Uncinula*) *necatoron* grapevines,
*Setospaeria* species on corn and lawns,
*Sphacelotheca reilinia* on corn,
*Thievaliopsis* species on soybeans and cotton,
*Tilletia* species on cereals,
*Ustilago* species on cereals, corn and sugar beet, and
*Venturia* species (scab) on apples and pear. (e.g. (z.B. *V. inaequalis* on apples).

The complexes according to the present invention may be formulated with further compounds showing an activity against insects, acaricids or nematodes in a manner known per se. Furthermore, it has proven to be particularly advantageous to provide a crystalline complex of thiophanate methyl with a compound A which is active against stinging, chewing, biting or sucking insects and other arthropods, or to formulate a crystalline complex together with at least such a further active ingredient which is active against stinging, chewing, biting or sucking insects and other arthropods. stinging, chewing, biting or sucking insects and other arthropods, include for example insects from the order of the Coleoptera, in particular *Phyllophaga* sp. such as *Phyllophaga cuyabana, Sternechus* sp. such as *Sternechus pingusi, Sternechuns subsignatus, Promecops* sp. such as *Promecops carinicollis, Aracanthus* sp. such as *Aracanthus morei*, and *Diabrotica* sp. such as *Diabrotica speciosa, Diabrotica longicornis, Diabrotica 12-punctata, Diabrotica virgifera;*
Lepidoptera, in particular *Elasmopalpus* sp. such as *Elasmopalpus lignosellus, Diloboderus* sp.,
Isoptera, in particular *Rhinotermitida,*
Homoptera, in particular *Dalbulus maidis,* and nematodes, including root-knot nematodes, for example *Meloidogyne* spp. such as *Meloidogyne hapla, Meloidogyne incognita, Meloidogyne javanica* and other *Meloidogyne* species; cyst-forming nematodes such as *Globodera rostochiensis* and other *Globodera* species; *Heterodera avenae, Heterodera glycines, Heterodera schachtii, Heterodera trifolii* and other *Heterodera* species; Gall nematodes, for example *Anguina* species; stem eelworms and foliar nematodes such as *Aphelenchoides* species.

For example, a formulation comprising a crystalline complex of pyraclostrobin and thiophanate-methyl may be used for combating of the following harmful fungi:

*Alternaria* sp. cereals, cotton and rice,
*Ascochyta* sp. on cotton and rice,
*Botryodiplodia* sp. on cotton,
*Cercospora* species on corn, soybeans, rice and various plants,
*Corynespora* sp. on soybeans, cotton and various plants,
*Colletotrichum* species on soybeans, cotton and various plants,
*Curvularia* sp. on cereals and rice,
*Diplodia* sp. on cereals and rice,
*Drechslera* sp. on cereals and rice,
*Fusarium* sp. on cereals, soybeans and cotton,
*Giberella* sp. on cereals and rice,
*Macrophomia* sp. soybeans and cotton,
*Penecilium* sp. on soybeans and cotton
*Phaeoisaripsis* sp. on soybeans,
*Phoma* sp. on soybeans,
*Phomopsis* sp. on soybeans,
*Pythium* sp. on soybeans and cotton,
*Pyrenophora* sp.
*Pyricularia* sp. on rice,
*Rhizoctonia* sp. on soya, rice and cotton,
*Rhychosporium* sp. on rice,
*Septoria* sp. on soya,
*Tilletia* sp. on cereals and rice,
*Ustilago* sp. on cereals.

For example, a formulation comprising crystalline complex of pyraclostrobin and thiophanate-methyl together with fipronil or an other GABA antagonist such as acetoprole, endosulfan, ethiprole, vaniliprole, pyrafluprole or pyriprole as a further ingredient may be used for combating one of the following harmful fungi as mentioned above and at the same time for combating insects, e.g.

Coleoptera, in particular *Phyllophaga* sp. such as *Phyllophaga cuyabana, Sternechus* sp. such as *Sternechus pingusi, Sternechuns subsignatus, Promecops* sp. such as *Promecops carinicollis, Aracanthus* sp. such as *Aracanthus morei*, and *Diabrotica* sp. such as *Diabrotica speciosa, Diabrotica longicornis, Diabrotica 12-punctata, Diabrotica virgifera, Oryzophagus* sp., and Lepidoptera, in particular *Elasmopalpus* sp. such as *Elasmopalpus lignosellus, Diloboderus* sp.

A formulation, comprising thiophanate methyl and epoxiconazole, may be used, e.g. for combating the following harmful fungi:

*Microdochium* sp. on cereals.
*Tilletia* sp. on cereals and rice,
*Ustilago* sp. on cereals.

A formulation, comprising thiophanate methyl and metconazole, may especially be used, e.g. for combating the following harmful fungi:

*Rhynchosporium* sp. on cereals.
*Sphacelotheca* sp. on corn,
*Septoria* sp. on soya.

The novel crystalline complexes allow the preparation of low-solvent or solvent-free aqueous suspension concentrates both of crystalline complex on its own and of the crystalline complexes with further crop protection agents, in particular the mixing partners indicated above. The solvent content, in particular the content of aromatic hydrocarbons, minus any antifreeze agents, is generally not more than 2% by weight of the suspension concentrate and is frequently below 2% by weight. The suspension concentrates according to the invention are distinguished in particular by better storage stability compared to the known suspension concentrates and suspoemulsion concentrates containing a compound A or a mixture of compound A with thiophanate methyl.

The figures and examples below serve to illustrate the invention and are not to be understood as limiting it.

Figure 2:
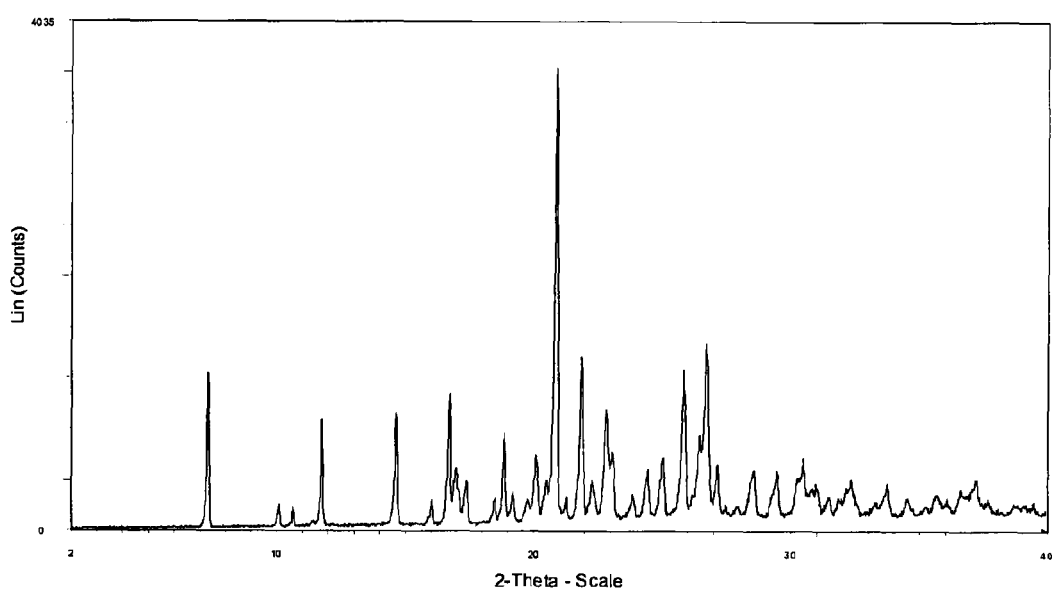
Figure 3:
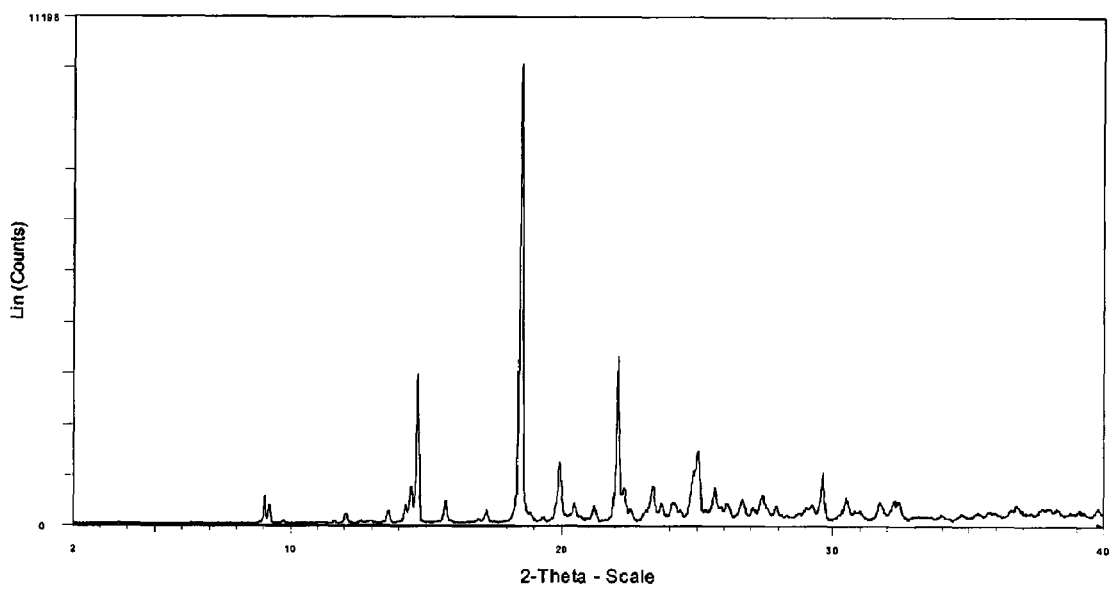
Figure 4:
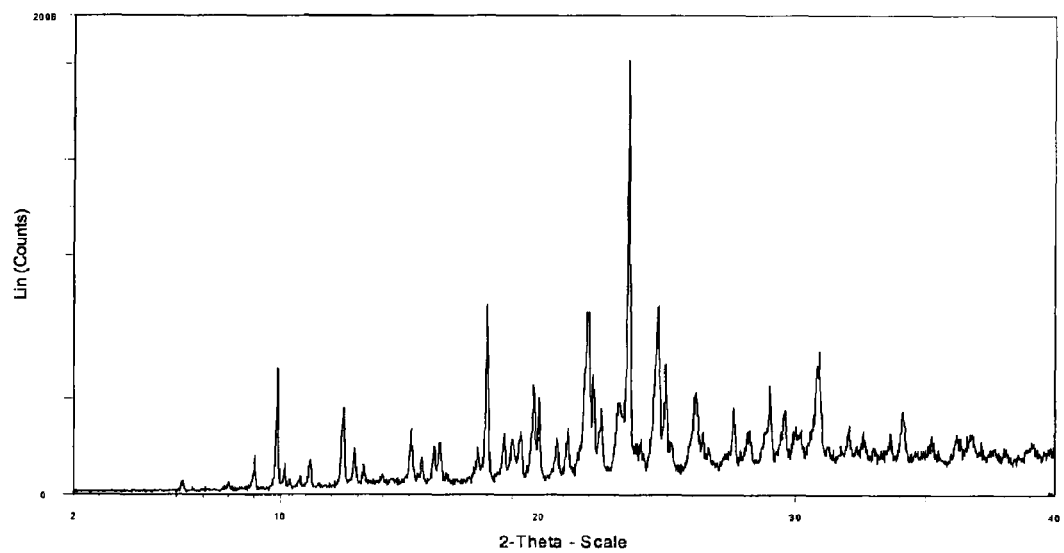
Figure 5A:
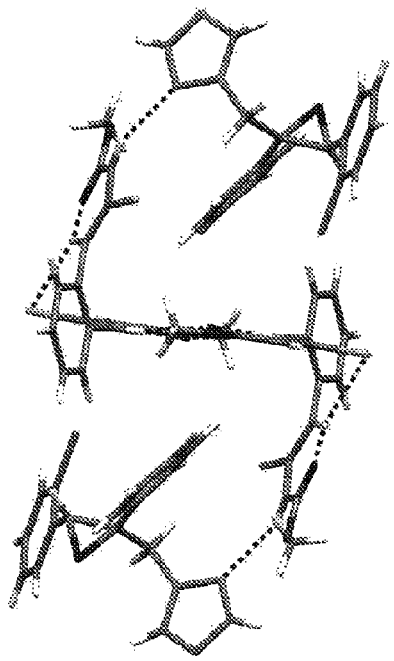
Figure 5B:
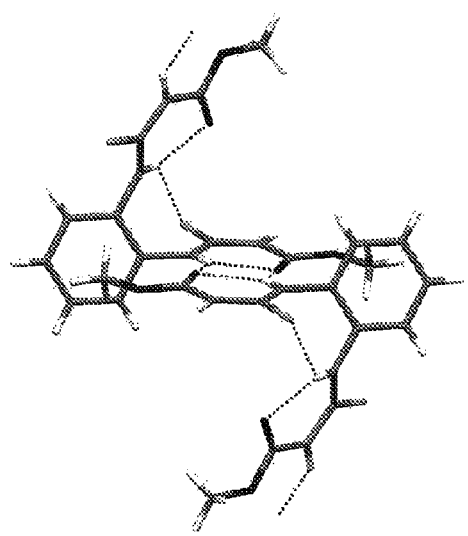
Figure 6:
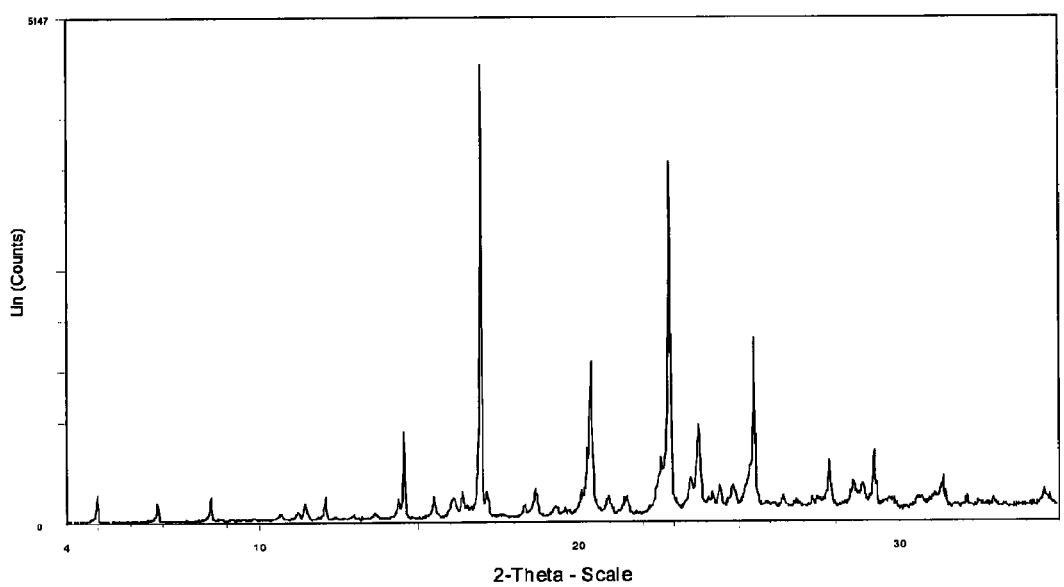
Figure 7:
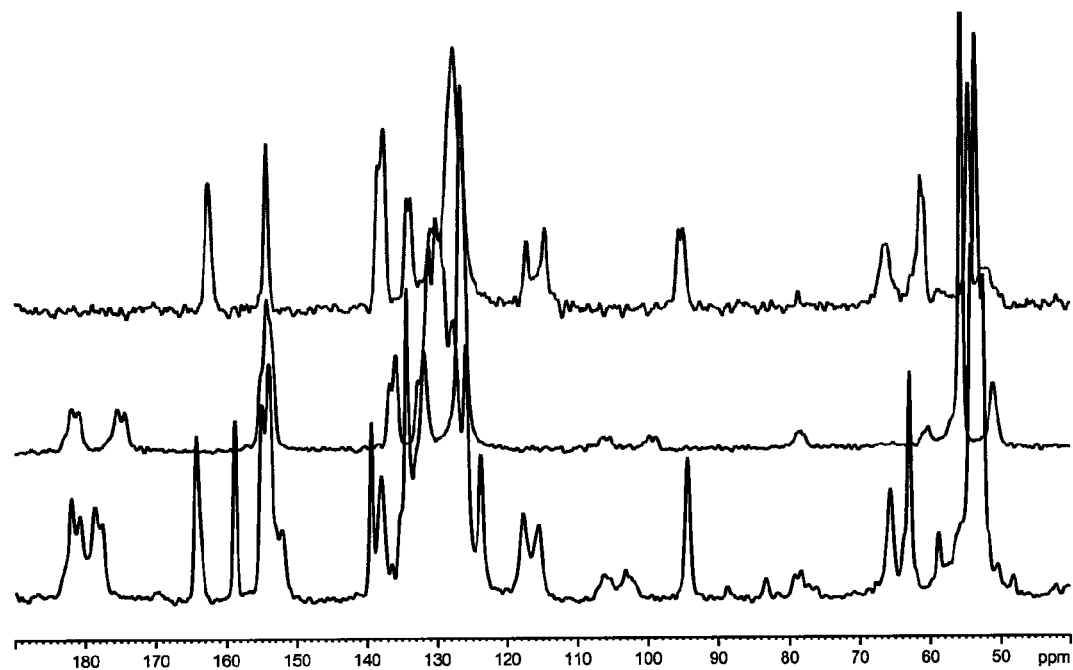
Figure 8:
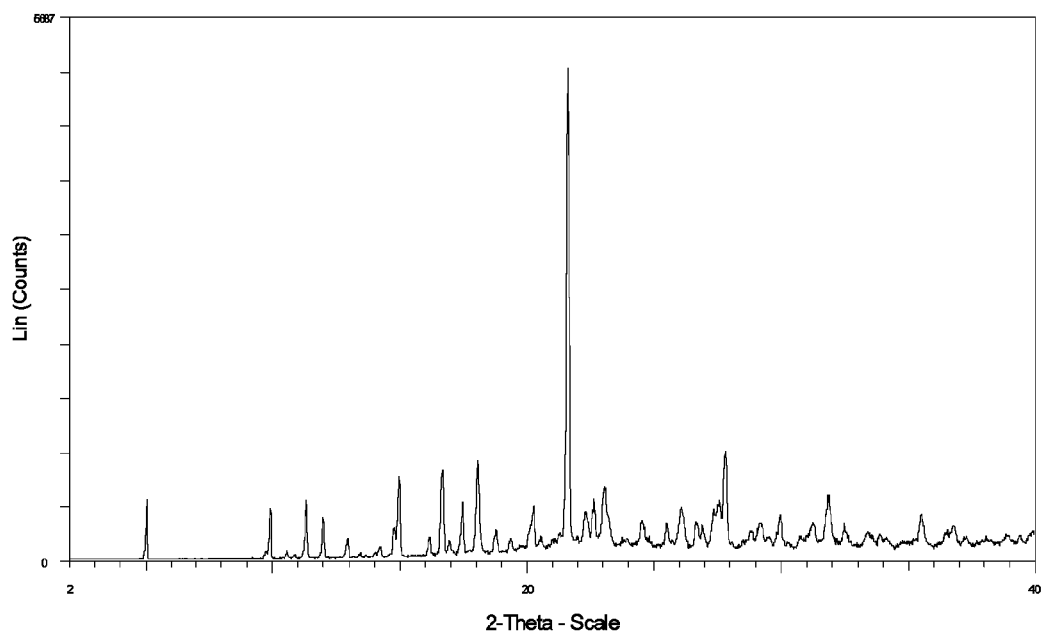
Figure 9:
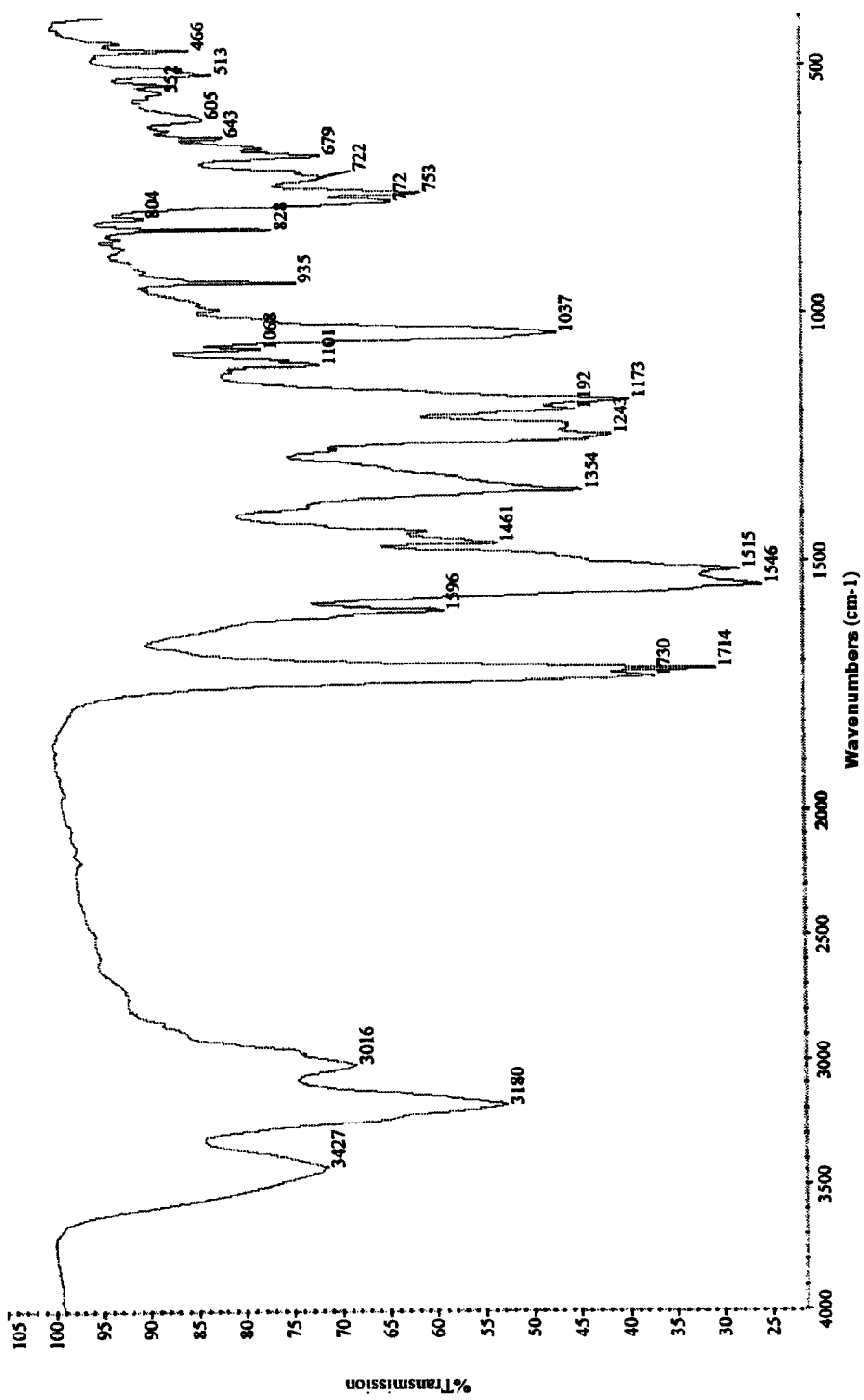
Figure 10:
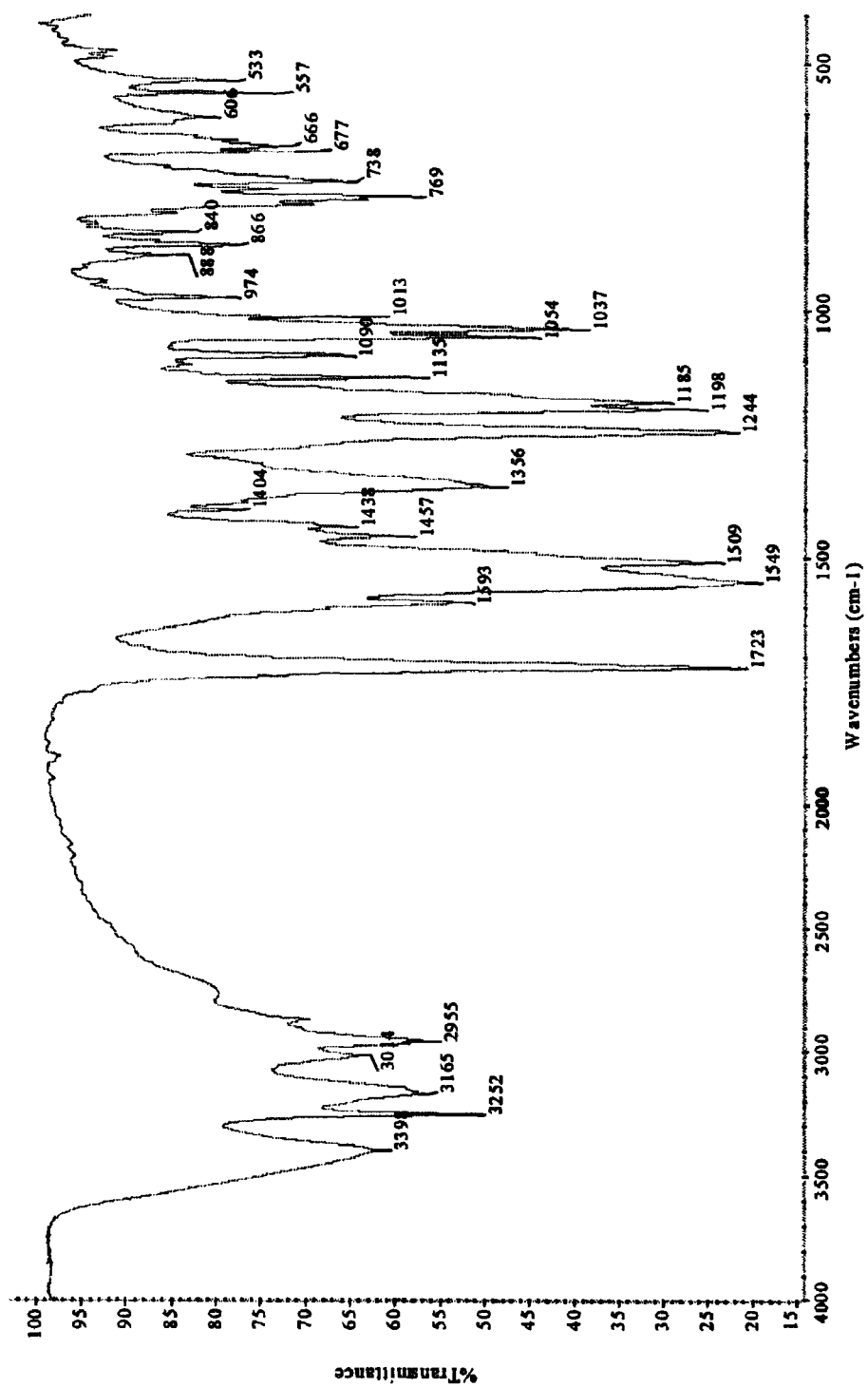

FIG. 1: X-ray powder diffractogram of thiophanate methyl.
FIG. 2: X-ray powder diffractogram of epoxiconazol.
FIG. 3: X-ray powder diffractogram of pyraclostrobin.
FIG. 4: X-ray powder diffractogram of the crystalline complex of thiophanate methyl and epoxiconazol.
FIG. 5a: Structure of the crystalline complex of thiophanate methyl and epoxiconazol according to X-ray analysis, of single crystals, with potential hydrogen bonds indicated.
FIG. 5b: Spatial arrangement of the thiophanate methyl molecules in the crystalline complex of thiophanate methyl and epoxiconazol according to X-ray analysis of single crystals, with potential hydrogen bonds indicated.
FIG. 6: X-ray powder diffractogram of the crystalline complex of thiophanate methyl and pyraclostrobin.
FIG. 7: $^{13}$C-CP/MAS spectra of pyraclostrobin (above), thiophanate methyl (middle) and the crystalline complex of thiophanate methyl and pyraclostrobin (below).
FIG. 8: X-ray powder diffractogram of the crystalline complex of thiophanate methyl and metconazol.
FIG. 9: IR-spectrum of the crystalline complex of pyraclostrobin and thiophanate methyl
FIG. 10: IR-spectrum of the crystalline complex of metconazol and thiophanate methyl

ANALYSIS

The pictures of the X-ray powder diffractograms (PXRD) were taken using a D-5000 diffractometer from Siemens in reflection geometry in the range from $2\theta=4°-35°$ with increments of $0.02°$ using Cu—K$\alpha$ radiation at 25° C. The $2\theta$ values found were used to calculate the stated interplanar spacing d.

Single crystal X-ray diffraction. The data were collected at 103(2) K on a Bruker AXS CCD Detector, using graphite-monochromated CuK$\alpha$ radiation ($\lambda=1.54178$ Å). The structure was solved with direct methods, refined, and expanded by using Fourier techniques with the SHELX-97 software package.

Thermogravimetric/differential thermal analyses were carried out with a Mettler Toledo TGA/SDTA 851 using $Al_2O_3$ as reference. The samples (8-22 mg) were placed in platinum sample cups for measurement. A temperature program from 30 to 605° C. at 10° C./min and N2 gas flow was used.

Differential scanning calorimetric determinations (DSC) were made on a Mettler Toledo DSC 823e with TS0801RO Sample Robot and TS08006C1 Gas Control. The measurements were done with heating rates 5° C./min from 30 to 185° C. using aluminum crucibles with pinholes.

$^{13}$C-CP/MAS measurements were run on a BRUKER Avance 300 instrument linked to a 7T wide bore magnet, $^{13}$C resonance frequency was 75.47 MHz. A Bruker MAS probe with 7 mm o.d. $ZrO_2$ rotors, spinning at 5700 Hz was used (this produces spinning side bands spaced 75.5 ppm from the isotropic signal). $^{13}$C spectra were generated by cross-polarization (Hartmann-Hahn contact 3 ms, $B_1$=45 kHz), acquisition time 35 ms, TPPM modulated decoupling ($B_1$=45 kHz) during acquisition, waiting time 2 s up to 120 s, depending on the suspected (or measured) longitudinal relaxation time $T_1$(H) of the protons; number of scans 500 to 10 000, depending on the waiting time used. The ppm scale was externally calibrated, setting the low field signal of adamantane to 38.066 ppm. A typical measurement, on the "mixed crystal" for example, involved 500 scans with a waiting time of 120 s between the scans, thus using a total time of measurement of 17 hrs.

The IR spectra of the samples were measured from KBr tablets on a Thermo Nicolet Nexus 470 IR spectrometer with a DTGS KBr detector.

The particle sizes in the suspension concentrates were determined using a Mastersizer 2000 from Malvern Instruments GmbH.

Epoxiconazol was used as a racemic mixture. It is known to exist in monoclincic crystalline form I that is thermodynamically stable at 22° C. A single crystal structure of Form I has been determined (monoclinic, space group P21/n, a=5.396 Å, b=17.304 Å, c=16.568 Å, β=91.742°). The experimental PXRD data is given in FIG. 2. Form I has a melting range from 130 to 140° C.

Thiophanate methyl is known to exist in monoclincic crystalline form that is thermodynamically stable at 22° C. X-ray analysis of single crystal reveals a monoclinic unit cell (space group P21/n) with dimensions a=10,715 Å, b=11,548 Å, c=11,548 Å and β=90,49°. Thiophanate-M decomposes directly after melting (m.p. ~180° C. for Form I).

Pyraclostrobin is known to exist in for different polymorphs as described in WO 2006/136357. For the following experiments, polymorph IV was used (see PXRD in FIG. 3).

PREPARATION EXAMPLES

I Slurry Method:

Example 1

1 g of thiophanate methyl and 1.13 g of epoxiconazol (1:1 molar ratio) were given in a round bottomed flask together with 20 ml of mixture of propanediol and water (1:3 v/v). The obtained slurry was stirred for one week at 50° C., after which the mixture was cooled to 22° C., filtered and dried at 22° C. on a clay plate. An PXRD revealed that the obtained crystalline material was a co-crystal of thiophanate methyl and epoxiconazol (FIG. 4). Melting of the crystalline complex begins at 148° C.

Examples 2 to 6

The process of example 1 was repeated by using different solvents or solvent water mixtures and applying different temperatures as given below:
Exp. 2: 1:3 glycerine:water (50° C.)
Exp. 3: 1:3 propylene carbonate:water (50° C.)
Exp. 4: 1:3 propylene carbonate:water (22° C.)
Exp. 5: 1:3 isopropanol:water (50° C.)
Exp. 6: Ethanol (22° C.)
In any of examples 2 to 6 a crystalline material was obtained, which was identified by PXRD as being the crystalline complex of thiophanate methyl and epoxiconazol.

Example 7

2 g of thiophanate methyl and 0.96 g of pyraclostrobin (2:1 molar ratio) were given in a round bottomed flask together with 20 ml of mixture of propanediol and water (1:3 v/v). The obtained slurry was stirred for one week at 50° C., after which the mixture was cooled to 22° C., filtered and dried at 22° C. on a clay plate. An PXRD revealed that the obtained crystalline material was a co-crystal of thiophanate methyl and pyraclostrobin (FIG. 5). The obtained material was identified by PXRD as being the crystalline complex of thiophanate methyl and pyraclostrobin.

Examples 8 to 10

The process of example 7 was repeated by using different solvents or solvent water mixtures and applying different temperatures as given below:
Exp. 8: 1:3 glycerine:water (50° C.)
Exp. 9: 1:3 propylene carbonate:water (50° C.)
Exp. 10: 1:3 propylene carbonate:water (22° C.)
In any of examples 8 to 10 a crystalline material was obtained, which was identified by PXRD as being the crystalline complex of thiophanate methyl and pyraclostrobin.

$^{13}$C-CP/MAS of the material obtained from examples 7 to 10 confirmed the presence of a co-crystal rather than a mixture of the individual crystalline materials. In particular, pyrachlostrobin and methylthiophanate relax with the same $T_1$(H): A presaturation of the $^1$H followed by a variable waiting delay allows for partial relaxation of the protons. This polarization was transferred from $^1$H to $^{13}$C via cross-polarization. The amplitudes of the $^{13}$C signals of pyrachlostrobin and of methylthiophanate then reflect the growing polarization of the $^1$H reservoir seen by each of the two types of molecules. Pyrachlostrobin and methylthiophanate showed identical $^1$H relaxation indication that both were coupled to the same $^1$H reservoir and thus must neighbors. The signals of both components relaxed identically, i.e. the whole spectrum scales as the $^1$H reservoir relaxes. Spectra taken at different delays (20 s and 120 s res.) were different by a factor of two in absolute intensity but fully fit onto each other after scaling. $T_1$ relaxation of the protons was 34.4 s (pure thiophanate methyl 28.6 s, pure pyraclostrobin 7.0 s).

Shear Method:

The following formulation additives were used:
Dispersant 1: Ethylene oxide/propylene oxide block copolymer (Pluronic PE 10500 of BASF Aktiengesellschaft).
Dispersant 2: Acrylic graft copolymer (Atlox 4913 of Uniquema).
Dispersant 3: Ethoxylated tristyrylphenol ammonium sulfate having 16 oxyethylene units: Soprophor 4D384 of Rhodia.
Dispersant 4: Sodium salt of the condensation product of phenolsulfonic acid and formaldehyde.
Defoamer: Commercial silicon defoamer (aqueous emulsion, 20% by weight of actives—Silfoam SRE obtained from Wacker Chemie AG.
Dye-formulation: Disperse Green Example 11 (Comparative)

A sample of 5 kg was prepared according to the recipe given in the following table (All amounts are given in g/kg). All components except the aqueous xanthan gum solution and disperse green were mixed in a vessel and then milled by two consecutive passes at 8 kg/h through a 600-ml bead-mill ran at a tip-speed of 6.7 m/s, while keeping the mixture at 20° C. To the obtained mixture the 2% solution of xanthan gum and the dye formulation were given with stirring. A homogeneous slightly viscous green opaque liquid was obtained. The particle size of this dispersion was determined by laser-diffraction on a 100-fold dilution in water to show 90% of the particles to have a size below 3.9 µm ($D_{90}$ value).

| | |
|---|---|
| Pyraclostrobin | 42 |
| Thiophanate-methyl | 378 |
| Glycerol | 70 |
| Dispersant 1 | 30 |
| Dispersant 2 | 19 |
| Dispersant 3 | 6 |
| Defoamer | 5 |
| Xanthan Gum (2% solution in water) | 55 |
| Dye formulation | 100 |
| water | 295 |

Example 12

A sample of 5 kg was prepared according to the recipe given in example 11. All components except the xanthan gum solution and disperse green were mixed in a vessel. This mixture was circulated at 20 kg/h for 8 hours through a 600 ml bead-mill ran at 6.8 m/s, while keeping the mixture at 40° C. To the obtained mixture the 2% solution of xanthan gum and the dye formulation were given with stirring. A homogeneous slightly viscous green opaque liquid was obtained. The particle size of this dispersion was determined according to example 11 to show a $D_{90}$ value of 1.3 µm.

A sample was evaporated to dryness. An PXRD of the obtained material revealed the presence of the crystalline complex of pyraclostrobin and thiophanate methyl besides excess thiophanate methyl.

Example 13 (Comparative)

A sample of 2 kg was prepared according to the recipe given in the following table (All amounts are given in g/kg). All components except the aqueous xanthan gum solution were mixed in a vessel. This mixture is cycled at 8 kg/h for 4 hours through a 600 ml bead-mill ran at 6.8 m/s, while keeping the mixture at 20° C. To the obtained mixture the 2% solution of xanthan gum was given with stirring. A homogeneous, slightly viscous. colourless opaque liquid was obtained. The particle size of this dispersion was determined according to example 11 to show a $D_{90}$ value of 1.4 µm.

| | |
|---|---|
| Pyraclostrobin | 42 |
| Thiophanate-methyl | 378 |
| Glycerol | 70 |
| Dispersant 1 | 30 |
| Dispersant 2 | 19 |
| Dispersant 3 | 6 |
| Defoamer | 5 |
| Xanthan Gum (2% solution in water) | 55 |
| water | 395 |

Example 14

A sample of 2 kg was prepared according to the same recipe and same procedure as in example 3, except that the mixture was heated to 45° C. before the milling was started and kept at this temperature during milling for 4 hours. A homogeneous, slightly viscous. colourless opaque liquid was obtained. The particle size of this dispersion was determined according to example 11 to show a $D_{90}$ value of 1.5 µm.

Storage Stability:

The stability of the samples produced in examples 1, 2, 3 and 4 were determined by storing a sub-sample of 100 ml in a HDPE bottle for a defined period at a defined temperature. A typical storage test would be for 8 weeks at 40° C. After storage, the particle size was determined both by laser-diffraction on a ~100-fold dilution and by determining the residue on a 150 µm wet-sieve.

Typically a good suspension quality is characterised by a $D_{90}$<10 µm and a wet-sieve residue that is <0.5%

| | $D_{90}$ | Wet sieve residue (150 µm Sieve) |
|---|---|---|
| Example 11 (comparative) | | |
| Fresh | 3.9 µm | 0.0% |
| After 8 weeks at 40° C. | 75 µm | 6.3% |
| Example 12 | | |
| Fresh | 1.3 µm | 0.0% |
| After 8 weeks at 40° C. | 6.0 µm | 0.0% |
| Example 13 (comparative) | | |
| Fresh | 1.4 µm | 0.0% |
| After 8 Weeks at 40° C. | 14 µm | 1.1% |
| Example 14 | | |
| Fresh | 1.5 µm | 0.0% |
| After 8 Weeks at 40° C. | 1.8 µm | 0.2% |

Example 15 (Comparative)

About 350 g of demineralised water were placed in a vessel. Thereto, 100 g of propylene glycol, 20 g of a dispersant 1, 30 g of dispersant 4, 2 g of a milling aid (amorphous silica) and 2 g of a defoamer (aq. emulsion of a silicon oil) were added. The mixture was stirred at 25° C. for 15 min. with a stirring speed of 1000 rpm. Then, 200 g of epoxiconazol and 300 g of thiophanate methyl were added with stirring at 1000 rpm. The mixture was then milled in a bead mill as described in example 11 until at least 80% by weight of the particles had a diameter below 2 µm, while keeping the mixture at 10° C. To the obtained mixture a 2% aqueous solution of xanthan gum and 2 g of a biocide formulation were added. A homogeneous slightly viscous liquid was obtained. The particle size of this dispersion was determined by laser-diffraction of a 100-fold dilution in water to show 80% of the particles to have a size below 2 µm ($D_{90}$ value). A PXRD of the solid showed a physical mixture of epoxiconazol and thiophanate methyl.

After 1 week storage at 60° C., the mixture became highly viscous and the laser-diffraction of a 100-fold dilution of the thickened liquid in water showed that less than 25% of the particles had a particle size below 2 µm ($D_{90}$ value).

Example 16

A formulation of epoxiconazol and thiophanate methyl was prepared according to the general recipe and similar to the procedure described in example 15, but performing the milling at 50° C. instead of 10° C. The particle size of this dispersion was determined by laser-diffraction of a 100-fold dilution in water to show 90% of the particles to have a size below 2 µm ($D_{90}$ value). A PXRD of the solids showed that the material was the crystalline complex of epoxiconazol and thiophanate methyl.

After 1 week storage at 60° C., the viscosity mixture was similar to the viscosity of the freshly prepared liquid and the laser-diffraction of a 100-fold dilution of the thickened liquid in water showed that 90% of the particles had a particle size below 2 μm ($D_{90}$ value).

Example 17

1 g of a mixture of metconazole and thiophanate-methyl (1:1 molar ratio) was placed in a round bottom flask and slurried in 20 ml of glycerine at 50° C. for 2 days. The mixture was cooled slowly to room temperature, filtrated and left to dry on a clay plate for some hours. The solid was analyzed by PXRD (see FIG. 8) to be >95-% pure co-crystals of metconazole and thiophanate-methyl. The DSC-measurement of the material showed an endothermic melting peak with onset at 155-158° C. and peak maximum at 160-168° C. The IR-spectrum is, shown in FIG. 10.

Example 18

2 g of a mixture of metconazole and thiophanate-methyl (1:1 molar ratio) was dissolved in 50 ml acetonitrile by gentle heating and stirring. The solution was filtered and the filtrate was left to evaporate in an open flask. After 1 day quadrate formed crystals large enough for single crystal X-ray analysis were achieved. The structure solution revealed a 1:1 co-crystal of metconazole and thiophanate-methyl. The experiment was repeated in ethyl acetate and nitromethane with similar results.

Example 19

32 parts by weight of thiophanate-methyl and 6 parts by weight of metconazole were slurried in a mixture of 50 parts by weight of water, 8 parts by weight of glycerine, 2 parts by weight of dispersant 1 and 2 parts by weight of dispersant 2. This mixture was mechanically milled in a colloid mill for 4 hours at 65° C. The slurry was left to cool down and after sedimentation of solid material the supernatant was decanted. The sediment was dried and analysed by IR to show the presence of co-crystal of thiophanate methyl and metconazol.

We claim:

1. A crystalline complex comprising thiophanate-methyl and pyraclostrobin, wherein, in an X-ray powder diffractogram at 25° C. and Cu—$K_\alpha$ radiation, shows at least four of the following reflexes, given as 2θ values: 4.9±0.2°, 6.8±0.2°, 8.5±0.2°, 12.0±0.2°, 14.5±0.2°, 16.9±0.2°, 20.4±0.2°, 22.9±0.2°, 25.5±0.2°, 29.3±0.2°.

2. A crystalline complex comprising thiophanate-methyl and epoxiconazole wherein, in an X-ray powder diffractogram at 25° C. and Cu—$K_\alpha$ radiation, shows at least four of the following reflexes, given as 2θ values: 6.2±0.2°, 9.0±0.2°, 9.8±0.2°, 12.4±0.2°, 15.1±0.2°, 18.0±0.2°, 21.9±0.2°, 23.5±0.2°, 24.7±0.2°, 30.9±0.2°.

3. A crystalline complex comprising thiophanate-methyl and metconazole, wherein, in an X-ray powder diffractogram at 25° C. and Cu—$K_\alpha$ radiation, shows at least four of the following reflexes, given as 2θ values: 5.0±0.2°, 9.9±0.2°, 11.3±0.2°, 12.0±0.2°, 15.0±0.2°, 16.7±0.2°, 18.1±0.2°, 21.6±0.2°, 27.8±0.2°.

4. A process for preparing the crystalline complex of claim 1, which comprises suspending thiophanate-methyl and pyraclostrobin in an organic solvent or in a mixture of water and an organic solvent.

5. A process for preparing the crystalline complex of claim 1, which comprises applying shear forces to liquid, which contains thiophanate-methyl and pyraclostrobin in the form of particles suspended in the liquid, at a temperature above 30° C. until the crystalline complex has been formed.

6. The process of claim 5, wherein shear forces are applied to an aqueous suspension containing thiophanate-methyl and pyraclostrobin in the form of particles suspended in an aqueous liquid.

7. An agricultural composition comprising, the crystalline complex of claim 1.

8. A process for preparing the crystalline complex of claim 2, which comprises suspending thiophanate-methyl and epoxiconazole in an organic solvent or in a mixture of water and an organic solvent.

9. A process for preparing the crystalline complex of claim 2, which comprises applying shear forces to liquid, which contains thiophanate-methyl and epoxiconazole in the form of particles suspended in the liquid, at a temperature above 30° C. until the crystalline complex has been formed.

10. The process of claim 9, wherein shear forces are applied to an aqueous suspension containing thiophanate-methyl and epoxiconazole in the form of particles suspended in an aqueous liquid.

11. An agricultural composition comprising, the crystalline complex of claim 2.

12. A process for preparing the crystalline complex of claim 3, which comprises suspending thiophanate-methyl and metconazole in an organic solvent or in a mixture of water and an organic solvent.

13. A process for preparing the crystalline complex of claim 3, which comprises applying shear forces to liquid, which contains thiophanate-methyl and metconazole in the form of particles suspended in the liquid, at a temperature above 30° C. until the crystalline complex has been formed.

14. The process of claim 13, wherein shear forces are applied to an aqueous suspension containing thiophanate-methyl and metconazole in the form of particles suspended in an aqueous liquid.

15. An agricultural composition comprising, the crystalline complex of claim 3.

* * * * *